(12) United States Patent
Mummy

(10) Patent No.: US 7,335,167 B1
(45) Date of Patent: Feb. 26, 2008

(54) POSTURE REALIGNMENT SYSTEM

(76) Inventor: Patrick Mummy, 8588 Villa La Jolla Dr., La Jolla, CA (US) 92037

( * ) Notice: Subject to any disclaimer, the term of this patent is extended or adjusted under 35 U.S.C. 154(b) by 450 days.

(21) Appl. No.: 11/127,409

(22) Filed: May 12, 2005

Related U.S. Application Data

(60) Provisional application No. 60/570,870, filed on May 12, 2004.

(51) Int. Cl.
  *A41H 1/02* (2006.01)
(52) U.S. Cl. .................. 600/587; 600/592; 600/594; 600/595; 33/512; 33/471; 73/1.75
(58) Field of Classification Search ............... 600/587, 600/592, 594, 595; 33/512, 471; 73/1.75
  See application file for complete search history.

(56) References Cited

U.S. PATENT DOCUMENTS

| | | | | |
|---|---|---|---|---|
| 2,023,539 A | * | 12/1935 | Packard | 33/423 |
| 4,201,226 A | * | 5/1980 | Phillips | 600/587 |
| 4,606,128 A | * | 8/1986 | Wyrwich et al. | 33/802 |
| 5,394,616 A | * | 3/1995 | Claxton | 33/275 R |
| 6,839,974 B1 | * | 1/2005 | Hitchcock | 33/473 |

* cited by examiner

*Primary Examiner*—Samchuan C. Yao
*Assistant Examiner*—Renee Danega
(74) *Attorney, Agent, or Firm*—Mintz, Levin, Cohn, Ferris, Glovsky & Popeo, P.C.

(57) ABSTRACT

A software system and apparatus for the collection of various measurements of the human body representing deviations from an ideal posture in several planes of motion relative to the body. A specially designed apparatus enables the correct measurements, while the software component performs an analysis of the measurements and recommends an exercise routine based on the severity of the deviations with respect to the planes of motion. The routine can be adjusted based on the flexibility and motivation of the patient as well as on the type of symptoms being experienced by the person. Additionally, physiologic factors are taken into account, such as the person's age and weight. The exercise routine is provided via a computer display, via email or via a web page available on the Internet, utilizing textual descriptions and visual and audio aids to describe the exercises.

12 Claims, 13 Drawing Sheets

FIG. 3

| Motivation 302 | | Flexibility 304 | | Pain 306 | | Ability 308 |
|---|---|---|---|---|---|---|
| Average | | Thoracic 311 | Average | Knee 316 | 6 | Expert |
| | | Groin 312 | Excellent | Back 318 | 8 | |
| | | Hamstring 313 | Poor | | | |

Routine 320

| Sequence 322 | Area 324 | Measurement Type 326 | Exercise 330 | | | | | Alternates 340 | Choices 350 | Exclusions 360 |
|---|---|---|---|---|---|---|---|---|---|---|
| | | | | Access 331 | Symmetry 333 | Type 335 | Ability 337 | Levers 339 | | | |
| 1) | Sagital | Illiac Crest | Static Floor | | | | | | Static Floor | Static Floor | None |
| | | | All | Bilateral | Passive | Everyone | 1 | | | |
| 2) | Transverse (2:1:1) | Illiac Crest | Piriformis Stretch (Wall) | | | | | | Static Floor | Static Floor | None |
| | | | All | Bilateral | Passive | Everyone | 1 | | | |
| 3) | Transverse (2:1:1) | PSIS-ASIS | Piriformis Stretch | | | | | | Static Floor | Static Floor | None |
| | | | All | Bilateral | Passive | Everyone | 1 | | | |

300

Transverse Plane
401

1. Iliac Crest Elevation
   a. <1° elevation = 0
   b. .5-2° elevation = 3
   c. 2.5-4° elevation = 6
   d. 4.5°+ elevation = 9
   403

2. PSIS-ASIS Differential
   a. <1° difference = 0
   b. .5-2° difference = 3
   c. 2.5-5° difference = 6
   d. 5.5°+ difference = 9
   407

3. Scapulae Elevation
   a. <1° elevation = 0
   b. .5-2° elevation = 3
   c. 2.5-4° elevation = 6
   d. 4.5°+ elevation = 9
   411

Frontal Plane
413

1. Pelvis Rotation (Right-Left/Left-Right)
   a. no rotation = 0
   b. slight rotation = 1
   c. medium rotation = 2
   d. large rotation = 3
   417

2. Torso Rotation (Right-Left/Left-Right)
   a. no rotation = 0
   b. slight rotation = 1
   c. medium rotation = 2
   d. large rotation = 3
   419

3. Forward Displacement (Pelvis, head, shoulders, knees)
   a. negative = 2
   b. 0" = 0
   c. 0.5-2" = 1
   d. 2-4" = 2
   e. 4-6" = 3
   f. 6"+ = 4
   421

4. Scapulae Protraction (Left/Right Scapulae)
   a. None (<5cm) = 0
   b. Slight (5-6cm) = 1
   c. Medium (6-7cm) = 2
   d. Large (7+) = 3
   423

FIG. 4A

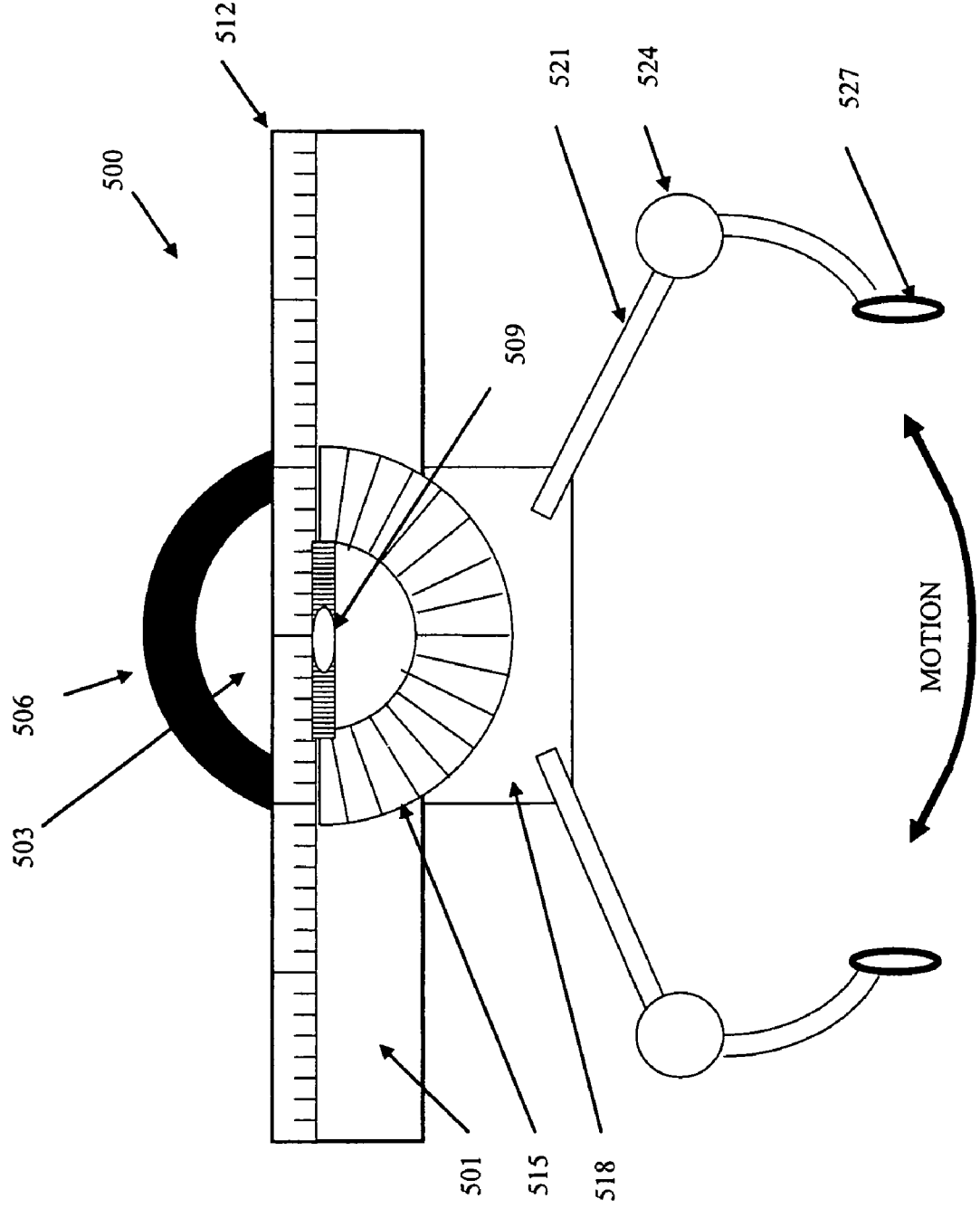

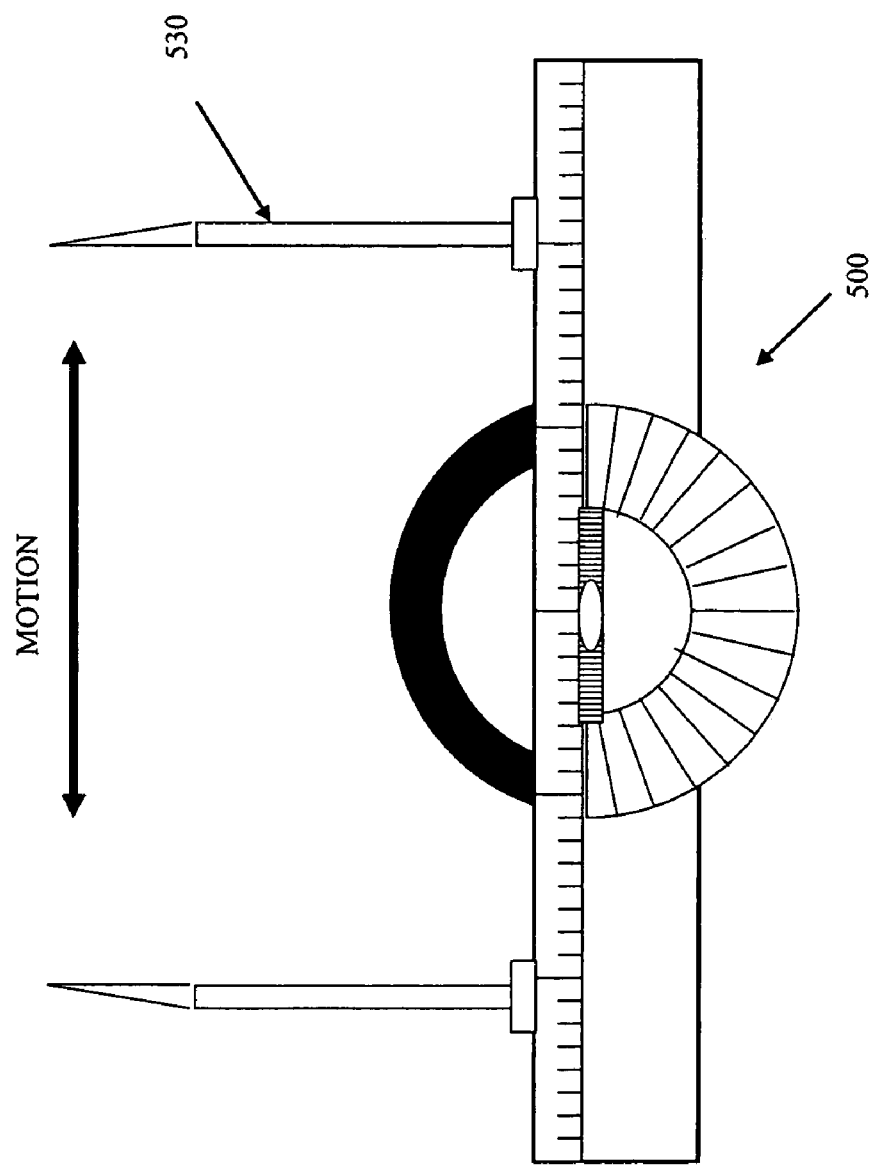

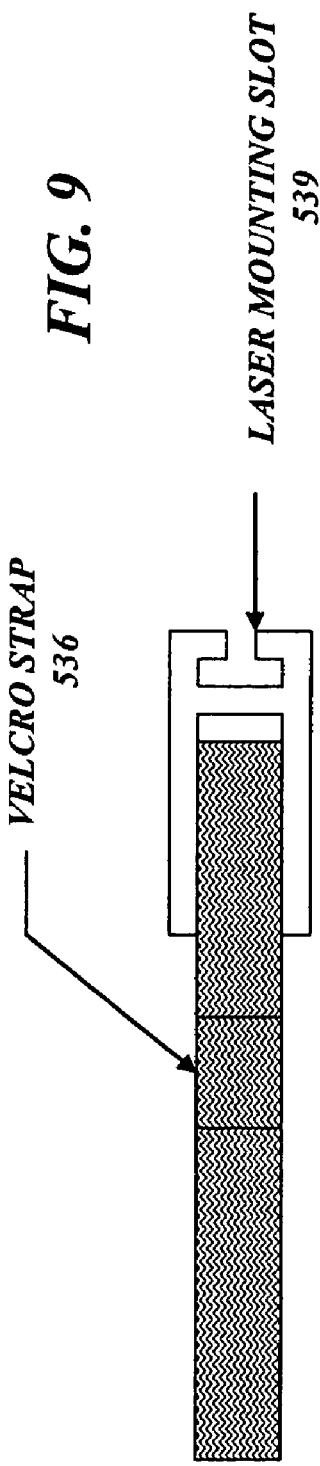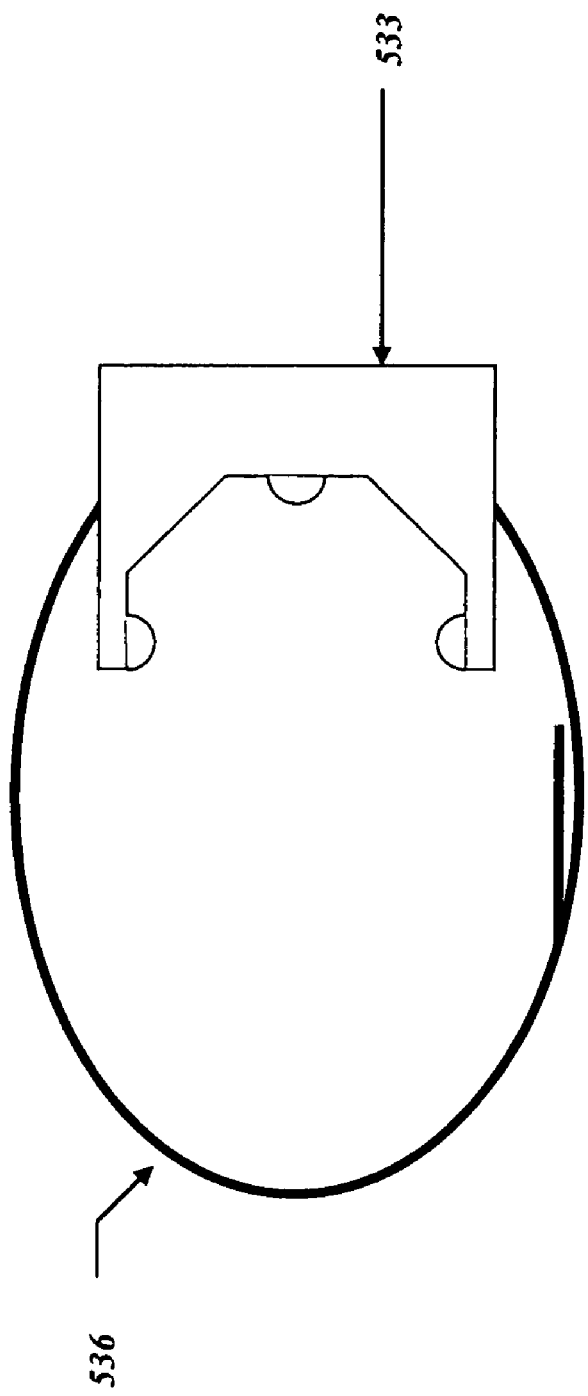

POSTURE REALIGNMENT SYSTEM

CROSS REFERENCE TO RELATED APPLICATIONS

This application claims the benefit of priority from U.S. Provisional Application No. 60/570,870, entitled "Physical Therapy Software System", filed May 12, 2004, which is incorporated herein in its entirety.

FIELD OF THE INVENTION

The present disclosure relates to posture realignment, and, in particular, to software and tools to assist in posture realignment.

BACKGROUND OF THE INVENTION

Posture for the human body can be described with respect to three planes of reference, as shown in FIG. 1A. When the planes' respective mid lines lie perpendicular to each other, the planes divide the body into equal sections, and indicate the body's center of mass at their intersection. For example, a sagittal plane, which is a vertical plane extending from the front of the body to the back, derives its name from the direction of the sagittal structure of the skull. The sagittal plane may also be considered as an anterior-posterior plane. A median plane, or mid-sagittal plane, can divide the body into equal left and right sides. A frontal plane, also known as coronal plane or lateral plane, is vertical to the body and extends from one side of the body to a opposite side of the body. The coronal plane derives its name from the direction of the coronal suture of the skull, and can divide the body into an anterior portion and posterior portion. A transverse plane is horizontal to the body and can divide the body into upper (cranial) and lower (caudal) portions.

Deviations of the body from any of these planes can adversely affect posture and can cause potentially damaging bodily compensations and dysfunctions, which may result in chronic pain for the patient. To correct these conditions, it is desirable that the tilt of the pelvic angle, which is an angle of the Posterior Superior Iliac Spine to the Anterior Superior Iliac Spine, be approximately 10 degrees. If the 10-degree tilt can be achieved, there can be a natural realignment of 90-degree angles of the skeleton relative to the planes of motion.

SUMMARY OF THE INVENTION

The present disclosure describes systems, methods, and techniques that assist in helping people posture issues and the chronic pain which may result therefrom.

In one embodiment of the invention, a software system uses one or more measurements of one or more landmarks of a person's body as it pertains to gravity. These measurement can indicate a plethora of problems in the alignment of the body with respect to the three planes shown in FIG. 1A. Based on these measurements, the system then suggests one or more exercises for a health care practitioner to recommend to that person to correct. The exercises may be performed by a patient at home, and the software can have visual representations of the recommended exercises, as well as audio instructions as to how the exercises should be done. For example, the visual representations may include pictures and video clips of a variety of isometric exercises. The software may also have voice instructions to guide the patient in the recommended exercises. In another embodiment of the invention, a method is implemented in software to help a person to align their body to reduce pain.

In other embodiments, the software generates a prescription of scientifically sequenced exercise routines that can be individually tailored for each patient's medical or fitness needs. The software may also be used to enhance the athletic performance of a patient. The software receives information for a patient from a health care practitioner user, identifies the problem with the patient, analyzes the information, and searches in a database of potential exercises to recommend to the patient. In some aspects, the software can evaluate data for the patient's physical alignment and prescribe individualized scientific therapeutic interventions to correct for deviations in the patient's alignment. The software can reduce practitioner error with patients and can help to ensure consistent results for patients. The software may also benefit the patient and the health care practitioner user by providing quick, convenient, and reliable solutions to address a patient's problems.

In still other embodiments of the invention, the software may be stored on one or more central servers and the health care practitioner user can conveniently and securely access the software and the database of potential exercises from any computer. The software can also store profiles, histories, and prescribed exercises of each patient. The software also helps to automate the process of selecting treatment programs, thereby allowing the health care practitioner user to handle more patients in a given amount of time.

The software system can also provide objective assessments in physical therapy and posture realignment. For example, a health care practitioner can evaluate a patient by visually assessing the patient's posture, and then treating the patient based upon this subjective analysis. The software system can use multiple measured and palpated triplanar skeletal landmarks to develop a comparable and quantifiable assessment. The patient's muscular system may have an inability to hold and move the patient's skeleton symmetrically in response to the force of gravity. Muscle testing, a traditional assessment technique, may determine the ineffectual firing of specific muscle groups. However, the disclosed software system has the benefits of providing a global skeletal assessment and/or a comparison to determine a cause of muscle dysfunction. Skeletal measurements entered into the software system can serve as objective and quantifiable measurements to allow a health care practitioner to specifically prescribe an individualized set of sequenced postural exercises to neuromuscularly re-educate holding patterns and movement patterns for the patient.

In another embodiment of the invention, the software system can generate individualized recommended exercises and stretches for patients of health care practitioners to obtain a 10-degree tilt when standing to allow the patient's skeleton to maintain the most effective and efficient posture with respect to the force of gravity. By using a software system that can use objective skeletal measurements for each patient, the patient's frame can be optimally positioned and moved against the force of gravity with the least amount of energy expended and with the most efficient means of movement.

Also described is a tool for performing various skeletal measurements of the patient. The tool can measure a number of bony landmarks, offsets, and displacements with respect to a plane of motion, such as a frontal plane, a transverse plane, or a sagittal plane. For example, some measurements may be taken that are associated with the transverse plane, such as the Iliac Crest (IC), the Anterior Superior Iliac Spine (ASIS), the Posterior Superior Iliac Spine (PSIS), and the scapulae. Other measurements taken can be associated with the coronal plane, such as scapular protraction, forward displacement, pelvic rotation, and upper torso rotation. Some other measurements can be taken that are associated with the sagittal plane, such as measurements related to an upper torso offset and the lower body, such as the legs and feet.

In some implementations, the measurement tool can include a plumb laser that is slidably attached to a level. The patient may stand against the backdrop of a wall, for example, and the plumb laser can be moved along the level to measure the posture and physical displacements of the patient's body. The tool can also include a protractor to measure angles of bodily rotation and displacement. The protractor is attached to the level substantially in the center thereof. The plumb laser and the level can be used to obtain measurements for the posture realignment software. When the measurements are obtained, they can be entered into the software's graphical user interface and can then be used to perform an analysis resulting in a treatment plan for the patient.

The health care practitioner can use the software to supplement their practice in their helping patients. The software is designed to be easy to use and learn, and can help the practitioners to learn the software system in a short amount of time.

Details of one or more embodiments are set forth in the accompanying drawings and the description below. Other features and advantages will be apparent from the description and drawings, and from the claims.

BRIEF DESCRIPTION OF THE DRAWINGS

FIG. 3 shows another portion of the user interface for a practitioner.

FIGS. 4A-4B shows a disparity severity chart with scaled values to be entered into the software.

FIG. 5 shows a top view of an exemplary tool for measuring patient data that includes rotating calipers.

FIG. 6 shows a top view of an exemplary tool for measuring patient data that includes sliding calipers.

FIG. 9 shows a side view of an exemplary knee mount attachment for a laser.

FIG. 10 shows a top view of an exemplary knee mount attachment for the laser.

DETAILED DESCRIPTION OF THE INVENTION

Figure 1:
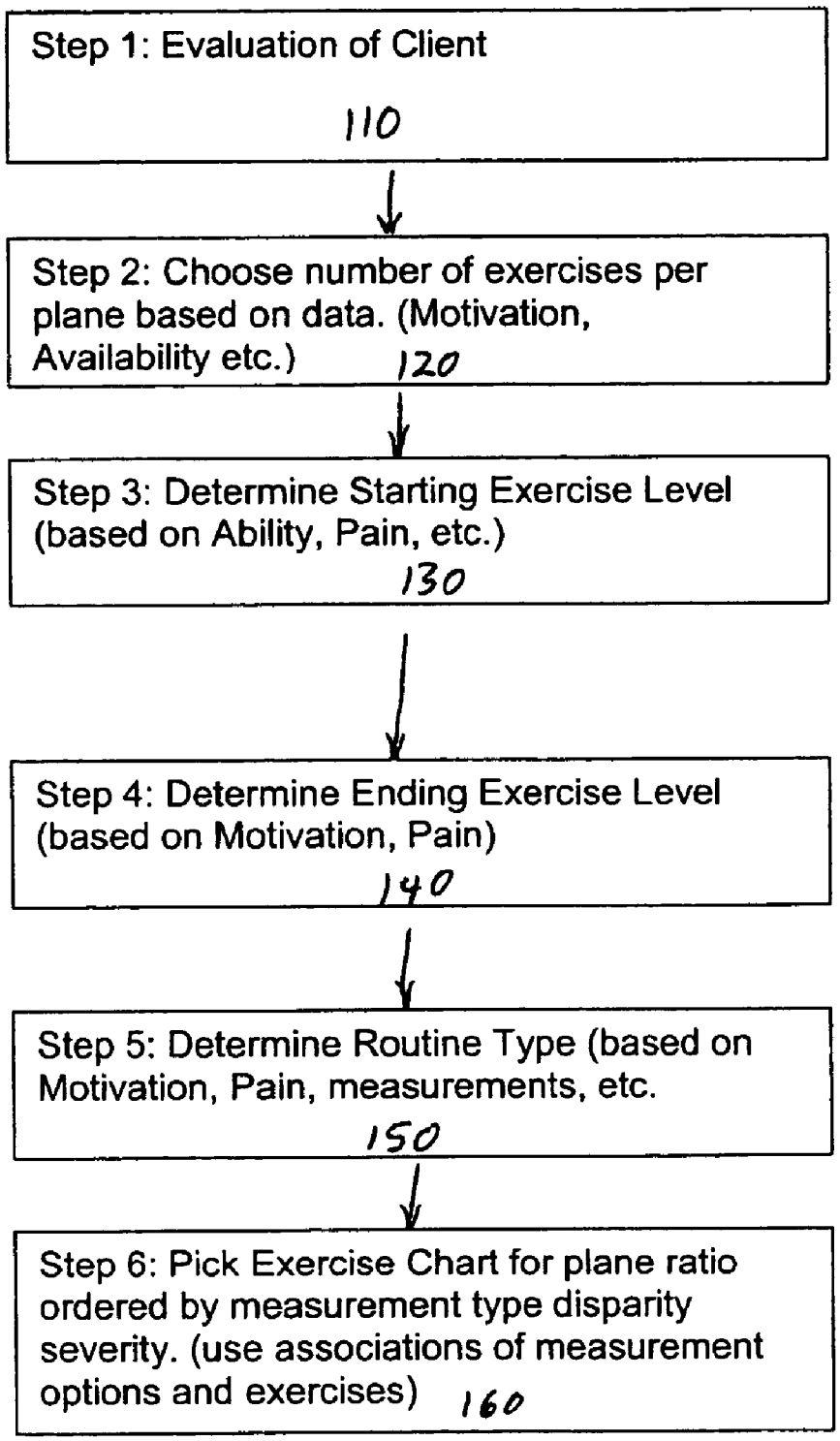
FIG. 1 shows a flowchart for using the posture realignment software system.

The following detailed description makes reference to the accompanying drawings. Other embodiments of the present disclosure are possible and modifications may be made to the embodiments without departing from the spirit and scope of the invention. Therefore, the following detailed description is not meant to limit the claims in any manner.

Moreover, for convenience in the ensuing description, some explanations of terms are provided herein. However, the explanations contained herein are intended to be exemplary only. They are not intended to limit the terms as they are described or referred to throughout the specification. Rather these explanations are meant to include any additional aspects and/or examples of the terms above and beyond the meaning of the terms to one of skill in the art.

The following describes various tasks, techniques, and systems relating to one or more methods implemented in software to perform posture analysis and help a health care practitioner to reduce the pain of a patient. The pain experienced by a patient may have any of a number of causes, such as an injury, a physical defect, an accident, and/or a misalignment of the body. Skeletal correctness can be considered our body's ideal skeletal alignment and a form our bodies are designed to maintain. Therefore, postural analysis can be performed by comparing a patient with an ideal skeletal alignment.

The "health care practitioner" may include those who are in the business of helping patients or clients to reduce pain. For example, those in the business of helping patients are osteopaths, general practitioners, message therapists, personal trainers, chiropractors, orthopedists, fitness and exercise experts, nutritionists, acupuncturists, and others in the medical and fitness professions.

The health care practitioner is the user of the software. The health care practitioner takes one or more measurements of the body of the patient, and enters those measurements into the software system. The software has one of more algorithms to process the measurements and utilize those measurements to formulate an exercise program that is suitable for the individual patient, based on that patient's measurements. For example, the software program may utilize a database of information that has a recommended exercise for certain measurements or sets of measurements. The exercises may be based on a particular part of the body, and/or may be based on the entire body. The recommended exercises are objectively quantifiable in that consistent recommendations can be based on the input of similar body measurements. Also, the recommended exercises may be customized for the measurements of a given patient. A representative sampling of recommended exercises is shown in the Appendix to this application. The preferred embodiment of the invention may use the list of exercises in the Appendix, however, an experienced practitioner may substitute other exercises for each category, based on professional experience as one of skill in the art, without deviating from the spirit of the invention. The software may be based on one or more methods to reduce pain, and may recommend one or more exercises to alleviate the pain.

The recommended exercises can be presented to the health care practitioner and/or the patient in a visual format, such as with a graphical user interface (GUI). The software may have pictures and video clips to demonstrate the exercises, as well as a voice-over to explain the exercise. For instance, when a health care practitioner enters the measurements in a the software system, the health care practitioner can show those recommended exercises to the patient while the patient is in the practitioner's office. Then, the patient can perform those recommended exercises at their convenience at home for a period of time (e.g., two weeks), and then return to the practitioner's office for a follow-up visit.

As the patient's body changes with subsequent exercises, the successive measurements will differ, and the software can recommend other or alternative exercises based on those measurements. The recommended exercises are based not only on the measurements taken by the practitioner and entered into the system, but also may be based on a number of other parameters, such as age, weight, height, and sizes of various portions of a patient's body, as further described herein.

FIG. 1 shows a flowchart 100 for using the posture realignment software system. The patient is evaluated (block 110) before entering values in the software. Based on the evaluation data from the patient, the practitioner can use the software system to choose a number or exercises per plane (block 120) for the patient. For example, the practitioner can assess the patient's motivation and/or availability for performing the recommended exercises and enter that data in the software. The evaluation data may also include the areas of pain for the patient and the flexibility of the patient. The practitioner may also enter measured data from one or more parts of the patient's body, such as weight, height, and the sizes of various body parts. The software can recommend a starting exercise level (block 130) and an ending exercise level (block 140) for the patient based on data that is entered from the evaluation. The software can also recommend an exercise routine (block 150) for the patient. The software can present one or more user interfaces that show recommended exercises, and charts of recommended exercises. For instance, the software can show an exercise chart (block 160) for a particular plane ratio based on the patient's measurements and evaluation data in a manner that will be discussed below.

Figure 1A:
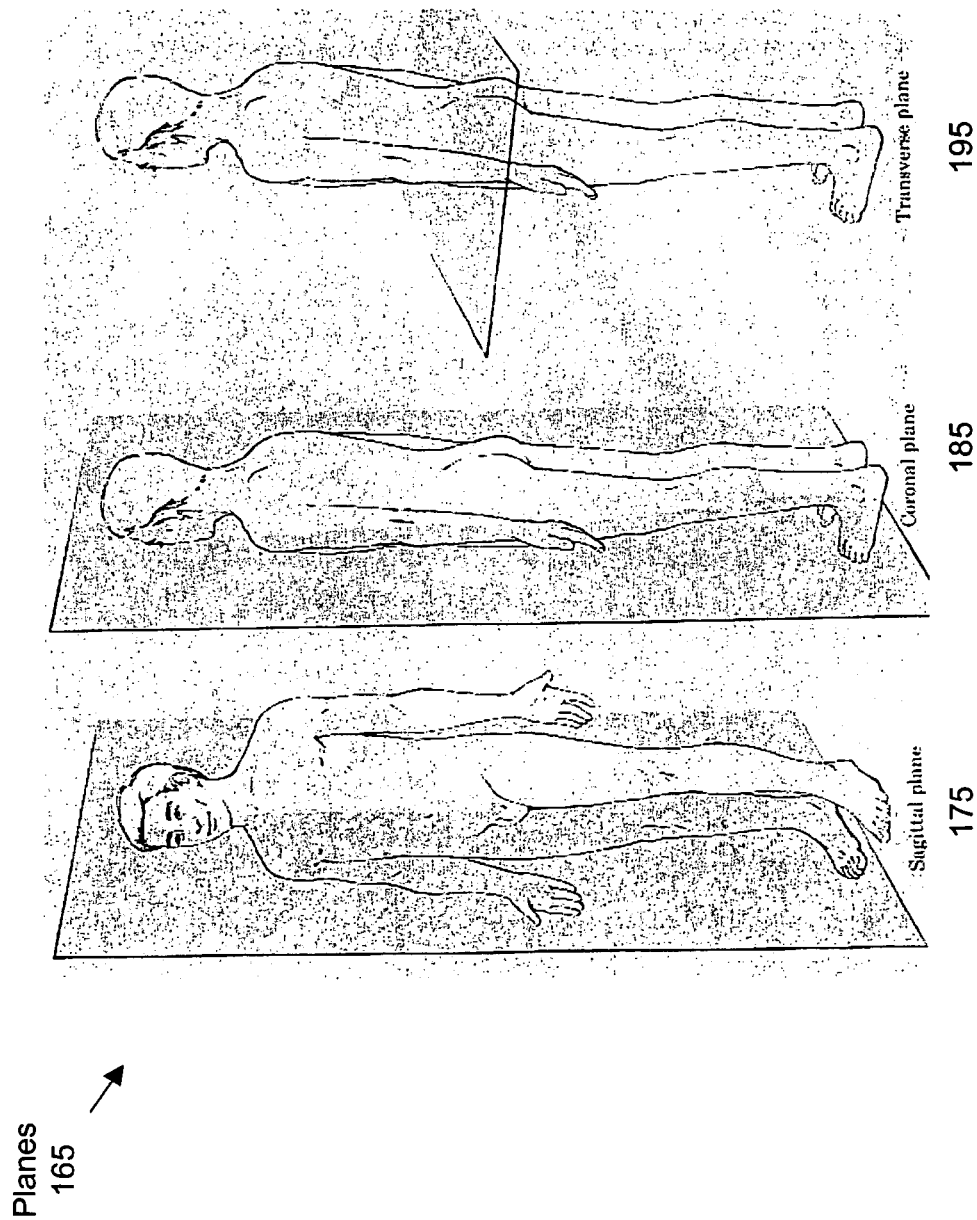
FIG. 1A shows exemplary diagrams of the frontal (coronal) plane, the transverse plane, and the sagittal plane.

FIG. 1A shows exemplary diagrams of planes 165, including the frontal plane 185, the transverse plane 195, and the sagittal plane 175. For purposes of this invention, the sagittal plane 175 refers to a plane approximately intersecting the left and right sides of the body. The frontal or coronal plane 185 refers to a plane approximately intersecting the front and back sides of the body. The transverse plane 195 refers to a plane approximately intersecting the upper and lower portions of the body. For purposes of collecting measurements of the body to be entered into the system, an ideal anatomical position of the body is an erect posture, face forward, arms at sides, palms of hands forward with fingers and thumbs in extension. The correct posture position can serve as a reference for definitions and descriptions of body planes and movements. It is designed as the "zero" position for measuring joint motions for most of the joints of the human body.

Figure 2:
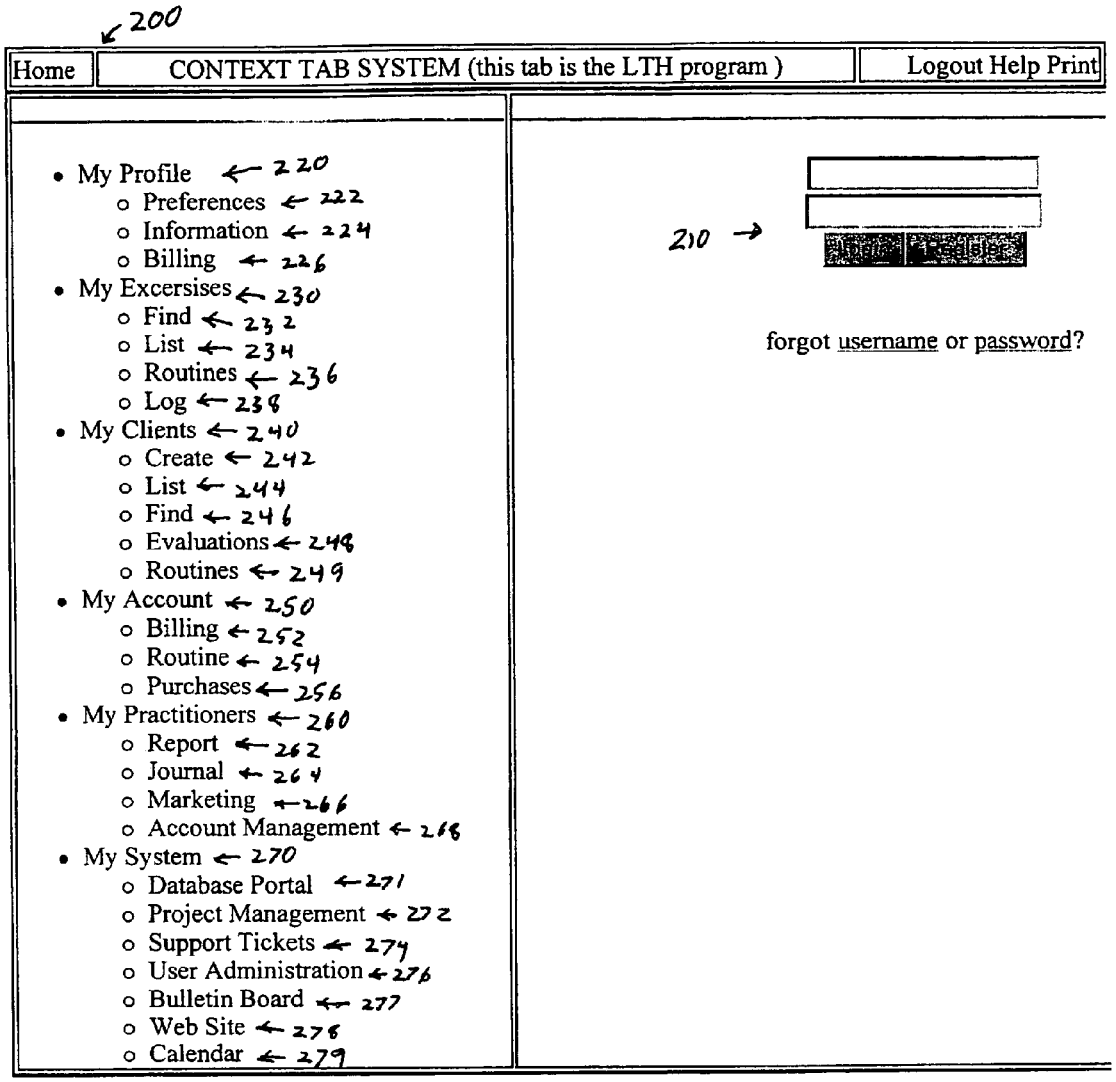
FIG. 2 shows a portion of the user interface for a practitioner.

FIG. 2 shows a portion of the graphical user interface 200 for a practitioner. To start a session for the software, the practitioner can login into and/or register with 210 the software. The software may have a profile 220 that is personalized for the practitioner with preferences 222, information 224, and billing 226. The software can present the recommended exercises 230 to the practitioner, along with a search tool 232, a list of exercises 234, routines 236, and a log 238 of exercise activities. New client profiles 240 can be created for new patients (242). The software also may list 244 and find 246 client profiles, as well as related patient evaluations 248 and routines 249. Financial account information 250 may be recorded, such as billings 252, routines 254, and purchases 256. The practitioner may also keep track of other practitioners 260 in his/her business with reports 262, journals 264, as well as marketing tools 266 and account management tools 268. The practitioner also has access to one or more of the following tools: database portal 271; project management tool 272; support tickets 274; user administration tools 276; bulletin boards 277; web sites 278; and related calendars 279.

FIG. 3 illustrates a screen 300 for patient data entry and evaluation. The software allows the user to enter the motivation 302 of the patient (e.g., poor, average, excellent), and the flexibility 304 of the patient. The flexibility 304 may involve an assessment of the flexibility of various body parts, such as the chest 311, the groin 312, and the hamstring 313. The patient's pain level 306 for various body parts may also be entered. For example, the practitioner may enter a pain level for a patient's knee 316 and back 318. The practitioner can also enter the patient's ability 308 to perform suggested exercises.

After the patient's evaluation data and/or measurements are entered, the software can recommend exercises and routines 320 in the graphical user interface. The software may have a database of exercises that can be recommended for patients based on a wide range of measurements and evaluation data. A sequence 322 of exercises 330 may be recommend for an area of the body 324 and a given measurement type 326. The software may offer alternative exercises 340 and choices 350 in the event the patient does not or could not perform the recommend exercise 330. The recommended exercises take into account the access 331, symmetry 333, type 335, and ability 337 of the exercise. A level 339 may also be shown that shows one or more calculation adjustments made in recommending the particular exercise to the patient. The software may also recommend exercises to exclude 360 for various body parts in the routine 320.

Figure 4:
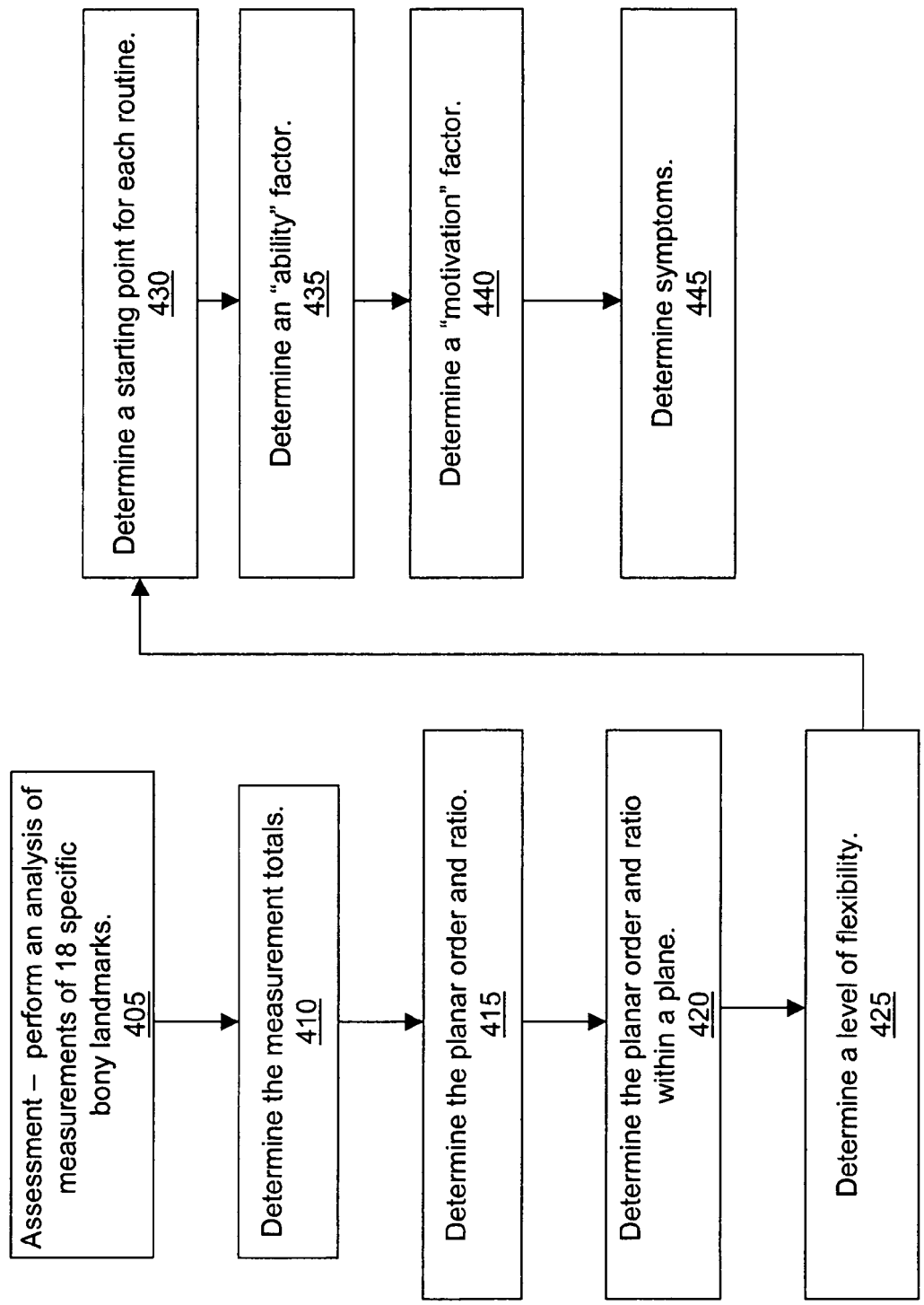
FIG. 4 shows an exemplary flow diagram for creating an exercise routine.
Figure 4B:
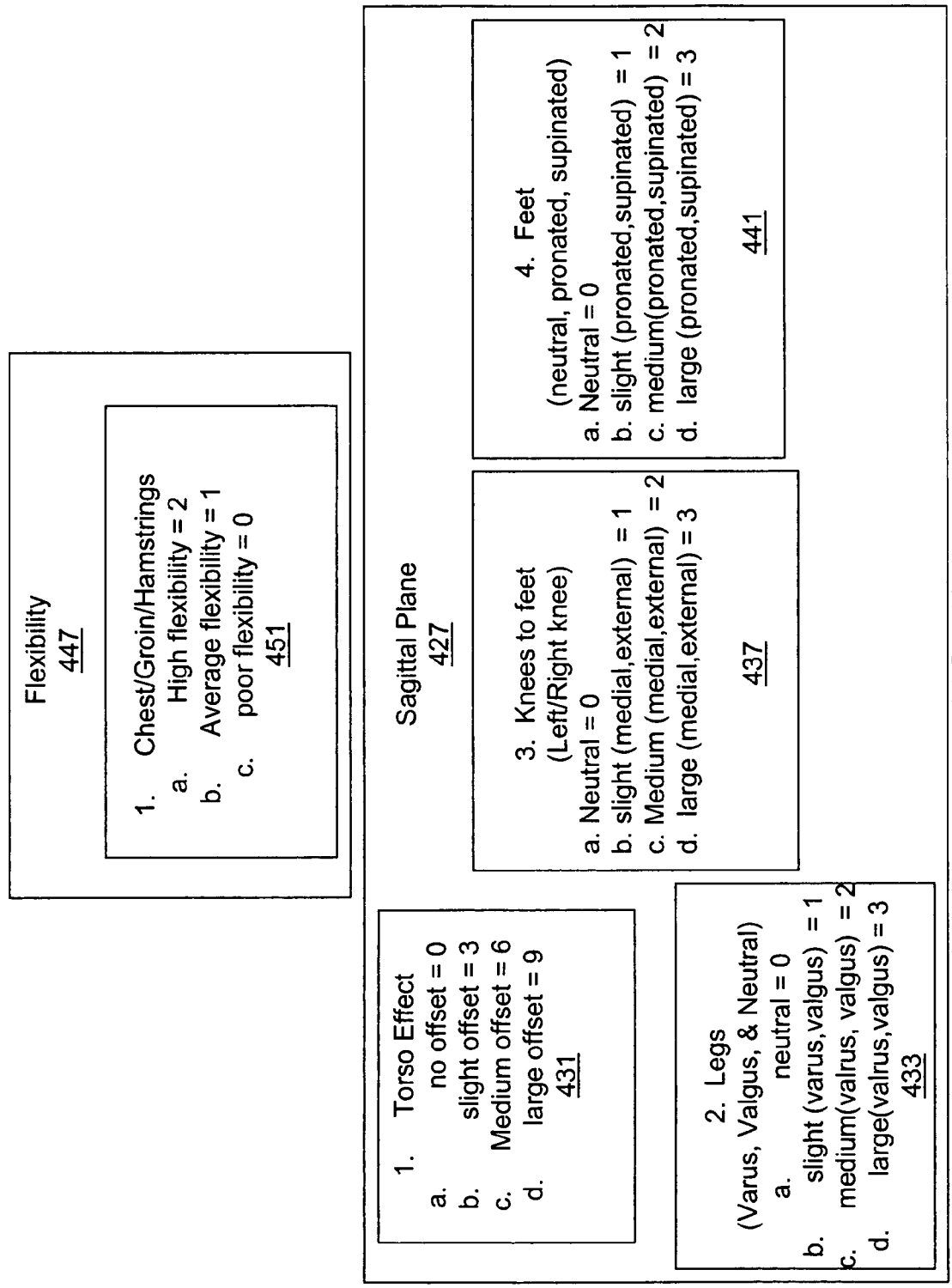

FIG. 4 shows an exemplary flow diagram for creating an exercise routine. Given objective measurements from the bony parts of the patient's body, the software can generate an individualized exercise routine. Some objective measurements may be taken from the measurement tool described herein. The first step in the flow diagram is performing an assessment (block 405) of the patient by taking the patient's measurements. In the preferred embodiment of the invention, there are 18 objective measurements which may be taken in performing the assessment (block 405). These measurements are described below and are also shown in FIGS. 4A and 4B. However, the actual number and type of measurements can vary.

In some implementations, the measurements may be taken by a measurement tool. The measurement tool can be used to measure bony landmarks associated with one or more planes of motion. In one embodiment of the invention, the measurement tool may include a plumb laser that is slidably attached to a level. The level may be one of various types of levels, such as a Johnson level, a mill level, an I-beam level, or an aluminum box level. In use, the patient stands against the backdrop of a wall and the plumb laser is moved along the level to measure the posture and physical displacements of the patient's body. The tool can also include a protractor to measure angles of bodily rotation, bending, and displacement, the protractor being attached to the level substantially in the center thereof. The tool can be used to obtain the measurements described below for the posture realignment software.

Figure 7:
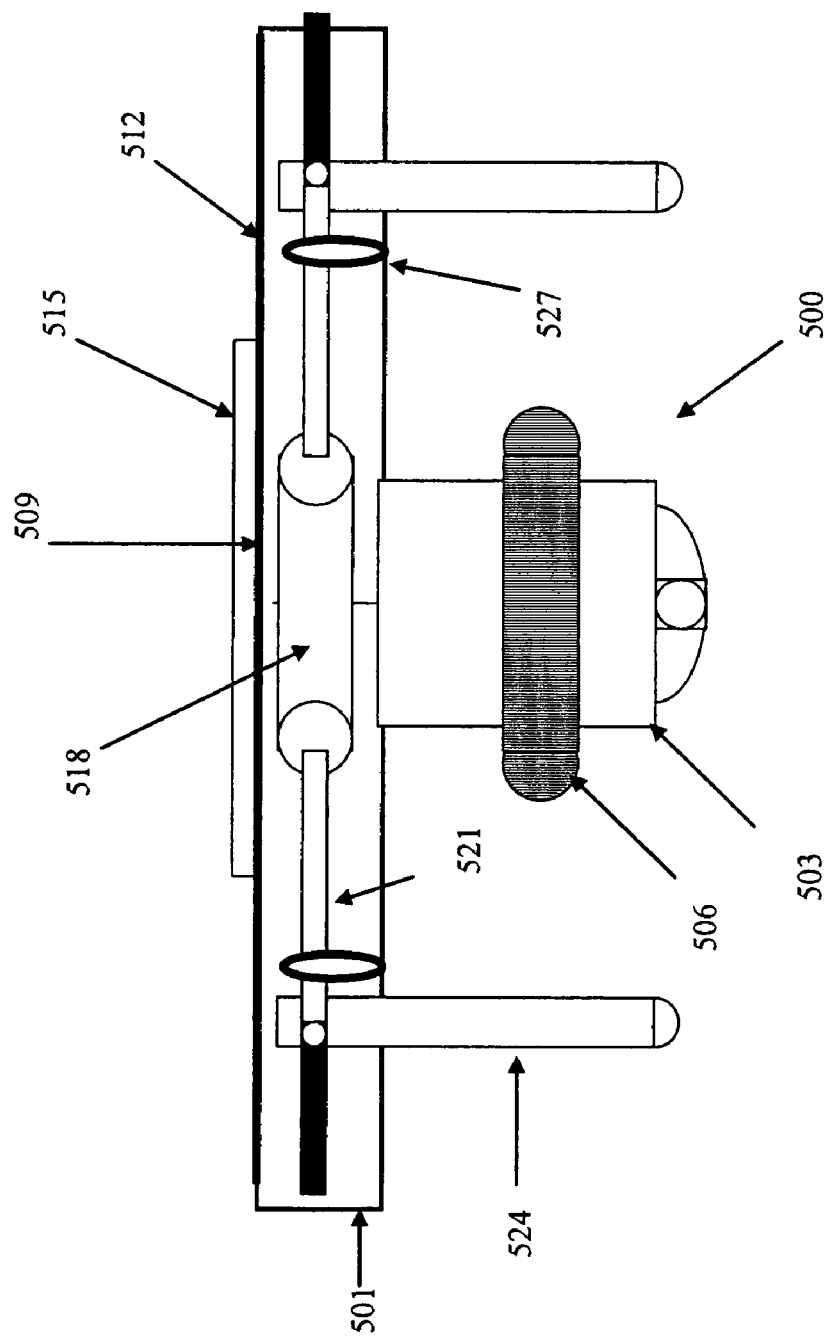
FIG. 7 shows a side view of an exemplary tool for measuring patient data that includes rotating calipers.

FIGS. 5-10 show implementations of a measurement tool for the posture realignment system. FIG. 5 shows a top view of an exemplary tool for measuring patient data that includes rotating calipers. A top view of the exemplary tool 500 is shown in FIG. 5 and a side elevational view is shown in FIG. 7. The tool includes a track 501 with a scale 512 and an attached protractor 515. The tool 500 includes a thumb ring 506 and a laser level 509 for the plumb laser. The tool includes rotating calipers with each rotating caliper having a finger ring 527, a handle 524, and a caliper arm 521. The caliper arm 521 is attached to a caliper carriage 518. The rotating calipers can be moved in a circular motion, and the angle of the rotating calipers can be measured by the protractor.

Figure 8:
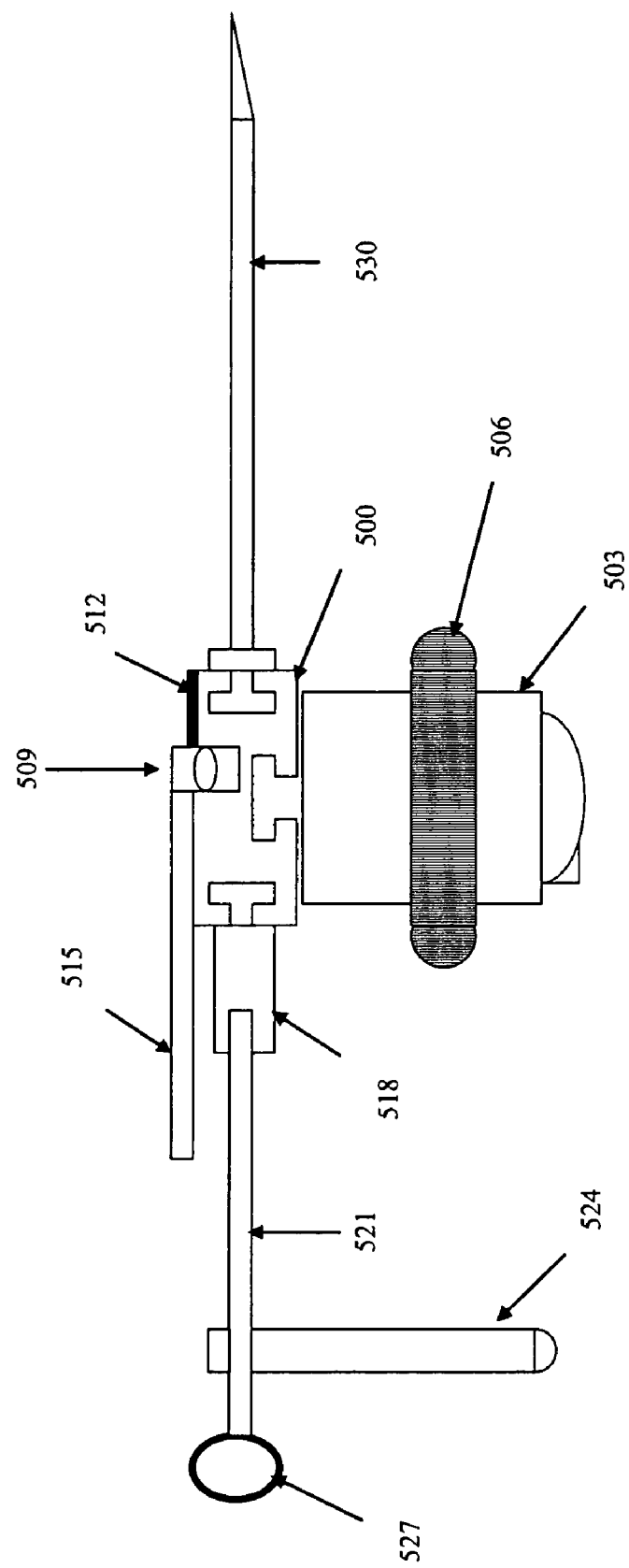
FIG. 8 shows a side view of an exemplary tool for measuring patient data that includes rotating calipers and sliding calipers.

FIG. 6 shows a top view and FIG. 8 shows a side elevational view of another embodiment of an exemplary tool for measuring patient data that includes sliding calipers 530. The sliding calipers 530 can be moved in a motion parallel to the track 501, and the scale 512 can be used to take measurements at the sliding caliper locations.

FIG. 9 shows a side view of an exemplary knee mount attachment for a laser that includes strap 536, which may be composed of Velcro, to secure the laser and a laser mount slot 539 for attaching to the tool shown in FIGS. 5-8. FIG. 10 shows a top view of the exemplary knee mount attachment for the laser.

The measurements taken by the tool implementations shown in FIGS. 5-10 may be taken with respect to one of the described planes of motion. For example, some measurements may be taken that are associated with the transverse plane, such as the Iliac Crest (IC), the Anterior Superior Iliac Spine (ASIS), Posterior Superior Iliac Spine (PSIS), and the scapulae. Descriptions of tool 500 shown in FIGS. 5-10 are provided below along with corresponding exemplary techniques for obtaining measurements for one or more landmarks.

The iliac crest refers to the long, curved upper border of the wing of the ilium. When the iliac crest is located, the measurement can be based on locating the same points on either side of the ilium. Each caliper arm 521 of tool 500 in FIG. 5 can be held at handle 524 in the palm of the hands with a tip of each forefinger inserted within finger rings 527 to provide stability when conducting the measurement. If the patient is small enough around the waist, the measurement can be taken from the front. The measurement can be taken by placing the tips of caliper arms 521 as far back on the crest as possible to get the best measurement. If the patient is too large around the waist, then the measurement can be taken from the back. In some cases, measuring from the back of the patient may result in the most accurate measurements. The endpoints of tool 500 can be moved in a side-to-side motion to displace any tissue or edema, until the same or a similar point on each bony landmark has been located. Measurements can be taken in degrees by reading level 509 on tool 500.

In some cases, the PSIS and ASIS measurements may be important measurements of the patient, as they may be the basis upon which all other measurements will be evaluated and compared. The ASIS can be an easy landmark to locate and therefore can be the first area to be palpated. The PSIS can be a more difficult landmark to locate due to the amount of attachments and tissue residing near this landmark. If the PSIS landmark is not easily located, then the PSIS landmark may be located by palpating the crest of the ilium from front to back until the posterior point is reached at which the gluteals are attached along the sacral iliac (SI) joint. Once the two points of the tool are in place, the measurer can displace both ends of the tool's tongs up and down along the two landmarks repeatedly until the midpoint of each have been located. The measurement can be conducted with the eyes of the patient closed or focused away from palpated area so as to produce a non-biased measurement. Each caliper arm 521 of tool 500 in FIG. 5 can be held at handle 524 in the palm of the hands with a tip of each forefinger inserted within finger rings 527 to provide stability when conducting the measurements. The endpoints of tool 500 can be moved in a up and down motion between the landmarks to displace tissue or edema, until the same or a similar point of each bony landmark has been located. Measurements can be taken in degrees by reading level 509 on tool 500. If the correct landmarks have not been located, then the measurements can be taken once and repeated again to make sure that the measurements are similar. In general, locating an exact location for measurements may not be as high of a priority as getting consistent measurements for each side.

Measurements associated with the scapulae also can be taken. One method to find the inferior border of the scapulae is to palpate a medial border of the scapulae and run fingers down until the bottom point is reached. Each caliper arm 521 of tool 500 in FIG. 5 can be held at handle 524 in the palm of the hands with a tip of each forefinger inserted within finger rings 527 to provide stability when conducting the measurements. Below the inferior border of the scapulae, the endpoints of tool 500 can be moved in a side-to-side motion between the landmarks to displace tissue or edema, until the same or similar point of each bony landmark has been located. Measurements can be taken in degrees by reading level 509 on tool 500. The measurement can be taken multiple times to ensure consistency.

In some measurements, the landmarks can first be located without the measuring tool, and the measurements can be taken with the patient's eyes closed before taking a reading from the measuring tool.

Other measurements taken can be associated with the coronal plane, such as scapular protraction, forward displacement, and pelvic rotation, and upper torso rotation. For the scapular protraction measurement, the medial border of the scapulae of a patient should be parallel to the spine and can be situated about two inches away from the spine. Any deviation measured from this laterally can be considered the amount of scapular protraction. The medial border of the scapulae can be palpated by running one or more fingers down the scapulae until just above the inferior border. The measurements can be taken using the sliding caliper arms 530 in a motion parallel to scale 512, as shown in FIG. 6. Each caliper arm 521 of tool 500 in FIG. 6 can be held by being straddled between a thumb and forefinger, with either an index finger or middle finger placed on an end of handle 524 to provide stability when conducting the measurements. One arm 530 of the tool 500 can be placed on a medial border of a spinous level and the measurement can be taken to an opposite arm 530 located at a medial border of the scapulae. The measurement between the arms 530 can be read from scale 512.

For the forward displacement measurement associated with the coronal plane, from the profile view, the coronal plane can be measured with a plumb line bisecting a lateral malleolus. The patient can have their eyes closed in order for the measurer to get an accurate measurement assessment. Once the patient has settled into position, a grid-lined wall or board with grid lines can be placed behind the patient to measure a distance forward of each bodily landmark, such as landmarks for a mid knee joint, a greater trochanter, a mid shoulder joint, and an ear. Instead of or in addition to using a grid behind the patient, stickers can be used on the landmarks to assist in measuring distances with a ruler. The measurements can be approximate and/or within a range, and do not have to be exact measurements.

Using laser plumb line 503 on top track 501 of tool 500, the laser can be positioned on the lateral malleolus while making sure the reading is set on "0" on scale 512. Using laser plumb line 503 attached on the top track 501 of tool 500, a measurement can start at the "0" mark on the scale lined up with the lateral malleolus and as the laser is slid across the grid, keeping track where each landmark (e.g., mid-knee joint, greater trochanter, mid deltoid, and ear-hole) falls on the ruler. Tool 500 can stay vertical while conducting the measurements.

The severity of the forward displacement can be classified as "slight", "medium" or "large". In some embodiments, a slight displacement can be less than 0-5 centimeters, a medium displacement can be 5 to 10 centimeters, and a large displacement can be larger than 10 centimeters.

Pelvic rotation around the coronal plane can be measured by kneeling in front of the patient with thumbs palpating the ASIS. For the pelvic rotation measurement, an assessment can be made in whether or not there is rotation of the pelvis and in which direction. The degree of rotation can based upon the assessment. For example, there can be a slight degree of rotation if the rotation is a little detectable. The degree of rotation can be medium if pelvic rotation is readily noticeable with palpitation, and the degree of rotation can be large if the pelvic rotation is noticeable without palpitation. In the same manner, assessments can be made on the upper torso to determine if the claviclular/pectoral area is rotated.

In conducting the measurements, the patient can stand with his or her feet together with his or her heels on a horizontal line on the floor, with a vertical line splitting the medial border of the feet. The ASIS of both illii can be palpated with the thumbs on tool 500 while staying square to the patient's feet. The direction of the rotation can be assessed. For example, if the patient's right hip is forward, then a "right to left" rotation can be selected.

Each caliper arm 521 of tool 500 in FIG. 5 can be held by being straddled between a thumb and forefinger, with either an index finger or middle finger placed on an end of handle 524 to provide stability when conducting the measurements. The forefingers can be placed on the ASIS to the left and right. Laser level 503 can be directed at a line at the 0-degree mark on protractor 515 and with the rotation. Thumbs can be placed in thumb ring 506 and the laser can be turned to match the vertical line on the floor. The severity of the pelvic rotation can be accessed and can be classified as "slight", "medium", or "large". In some implementations, a slight rotation can be less than 5 degrees, a medium rotation can be 5 to 10 degrees, and a large rotation can be larger than 10 degrees.

Upper torso rotation around the coronal plane can be measured by having the patient stand with his or her feet together with his or her heels on the horizontal line on the floor, with the vertical line splitting the medial border of the feet. One way to stay square to the patient's feet is to palpate both sides of a clavicular notch with the thumbs.

The direction of the upper torso rotation can be assessed. For example, if the patient's right torso is forward, then a "right to left" rotation can be selected. Each caliper arm 521 of tool 500 in FIG. 5 can be held by being straddled between a thumb and forefinger, with either an index finger or middle finger placed on an end of handle 524 to provide stability when conducting the measurements. The forefingers can be placed on the ASIS to the left and right. Forefingers can be placed on the clavicular notches to the left and right. Laser level 503 can be directed at a line at the 0-degree mark on protractor 515 and with the rotation. Thumbs can be placed in thumb ring 506 and the laser can be turned to match the vertical line on the floor.

The severity of the upper torso rotation can be assessed and classified as "slight", "medium" or "large". In some implementations, a slight rotation can be less than 5 degrees, a medium rotation can be 5 to 10 degrees, and a large rotation can be larger than 10 degrees.

Other measurements can be taken that are associated with the sagittal plane, such as measurements related to an upper torso offset and with the lower body, such as the legs and feet. For the upper torso offset measurement(s), the patient can be measured by facing the measurer behind the plumb line with a string bisecting the patient's feet. A major indication of an offset, other than by the nose not bisecting the string, can be a comparison of a distance of each arm from the side of the torso. For example, a patient with a sagittal offset may have a noticeable disparity between these distances (e.g., one arm falling further away from the torso than the other).

The measurer can palpate the spine from the first cervical vertebrae and down the vertebral column to determine if there are any major lateral shifts. The area which has the offset can be noted, as well as the degree of the offset. For example, one segmental component with a slight shift may be considered a "slight" offset. In some cases, slight offsets may only be detected with palpation. A double offset, or two slight offsets, can be considered a "medium" offset, even if the double offsets are slight. A segmental or total shift that can be easily noticeable with palpation may also be considered a "medium" offset. Medium offsets may be easily noticeable with palpation. "Large" offsets may be easily detectable without palpating.

There can be at least three areas to assess in the lower body when dealing with sagittal deviations: the legs as a whole, the knees, and the feet. In measuring the legs as a whole, the patient can stand and line up from the hip joint down to the ankle joint (neutral alignment). The assessment can show a varus stress (e.g., bowleggedness) or a valgus stress (e.g., knock-kneed). In some implementations, if the knee joints are in line with the hip and ankle, then the deviation is "neutral". If the knee joints are aligned inside of the hip and ankle then there can be valgus stress, and if the knee joints are aligned outside of the hip and ankle then there can be varus stress.

Using the laser level 503 attached on track 501 of tool 500, measurements can be started at the "0" mark on the scale lined up with the midline of the posterior knee joint and the laser can be moved while staying aligned with the midline of the knee joint. The laser can stay vertical by using level 509 on the tool.

The degree of the disparities can be assessed for the legs as a whole, using "slight", "medium", and "large" categories for the level of severity. In some implementations, a slight disparity can be where the midline of the knee joint is 2.5 centimeters from the starting point, a medium disparity can be where the midline of the knee joint is 2.5 to 5 centimeters from the starting point, and a large disparity can be one that is more than 5 centimeters from the starting point.

The degree of the disparities can be assessed for sagittal deviations for the legs around the knees. For example, in relationship to the feet, the knees can be considered "neutral", "medial", or "external". Another degree of disparity can be a degree of abduction of the feet and knees themselves. The relationship between the feet and knees may be neutral with each other, but abducted away from the sagittal line. In some cases, the relationship between the knee and the foot may be important in evaluating the sagittal disparities and may account correctly for the true disparity.

Strap 536, which, in the preferred embodiment is composed of Velcro, (FIGS. 9-10) can be placed on the knee so that the laser mounted in block 533 holding laser mounting slot 539, can display a 90 degree line or a line perpendicular to the face of the patellae. Thumbs can be inserted into thumb rings 506 and the laser can be turned to align with a vertical line through the foot.

In assessing the degree of the disparities of sagittal deviations for the legs around the knees, a "slight rotation" can be less than 5 degrees, a medium rotation can be between 5 to 10 degrees, and a large rotation can be larger than 10 degrees.

The feet can be assessed as well. For example, the feet may be considered pronated (inverted), supinated (everted), or neutral. The degree of the disparities of the feet may also be assessed as "slight", "medium" or "large". A slight disparity can be one that is difficult to notice. The foot can be slightly collapsed inwards or slightly rolled outwards for a slight disparity. A medium disparity can be rather easily seen, but may not be too overtly noticeable. A large disparity can be very noticeable. The foot can be very noticeably collapsed inwards or rolled outwards for a large disparity.

FIGS. 4A-4B show a disparity severity chart with variables from the measurements and a scale for each measurement that can be entered into the software system. In most cases, variables may be weighted on a scale of zero to three. Or example, the traverse plane and the torso offset may be multiplied by three to stay equally weighted to the other measurements. The assessments and scales used in FIGS. 4A-4B are not limited to the numbers and scaling shown, but may vary.

For the assessments in the transverse plane 401 in FIG. 4A, the iliac crest elevation 403, the PSIS-ASIS differential 407, and the scapulae elevation 411 all have a scale from zero to nine. Assessments for the iliac crest elevation 403 use a scale from zero to nine with "less than 1° elevation"="0", "0.5-2° elevation"="3", "2.5-4° elevation"="6", and "4.5° and greater elevation"="9". Assessments for the PSIS-ASIS differential 407 use a scale from zero to nine with "less than 1° difference"="0", "40.5-2° difference"=3, "2.5-4° difference"="6", and "4.5° and greater difference"="9". Assessments for the scapulae elevation 411 elevation 403 use a scale from zero to nine with "less than 1° elevation"="0", "0.5-2° elevation"="3", "2.5-4° elevation"="6" and "4.5° and greater elevation"="9".

For the assessments for the frontal plane 413 in FIG. 4B, the pelvis rotation, torso rotation, and scapulae protraction all have a scale from zero to three, and the forward displacement 421 has a scale from zero to four. Assessments for the pelvis rotation 417 (e.g., right to left or left to right) use a scale from zero to three with "no rotation"="0", "slight rotation"="1", "medium rotation"="2", and "large rotation"="3". Assessments for the torso rotation 419 (e.g., right to left or left to right) use a scale from zero to three with "no rotation"=" ", "slight rotation"="2", "medium rotation"="3", and "large rotation"="3". Assessments for the scapulae protraction 423 (e.g., left/right scapulae) use a scale from zero to three with "none (<5 cm)"="0", "slight (5-6 cm)"="1", "medium (6-7 cm)"="2", and "large (>7 cm)"="3". Assessments for the forward displacement 421 (e.g., pelvis, head, shoulders, knees) use a scale from zero to four with a "negative displacement"="2", "0 inch displacement"="0", "0.5-2 inch displacement"="1", "2-4 inch displacement"="2", "4-6 inch displacement"="3", and "greater than 6 inch displacement"="4".

The assessments for the sagittal plane 427 in FIG. 4B, the feet 441, legs as a whole 433, and an area of the legs from knees to feet 437 all use a scale from zero to three, and the torso effect 431 uses a scale from zero to nine. Assessments for the torso effect 431 use a scale from zero to nine with "no offset"="0", "slight offset"="3", "medium offset"="6", and "large offset"="9". Assessments for the legs as a whole 433 use a scale from zero to three with "neutral"="0", "slight (for varus or valgus)"="1", "medium (for varus or valgus)"="2", "large (for varus or valgus)"="3". Assessments for the area of the knees to the feet 437 use a scale from zero to three with "neutral"="0", "slight (for medial or external)"="1", "medium (for medial or external)"="2", and "large (for medial or external)"="3". Assessments for the feet 441 use a scale from zero to three with "neutral"="0", "slight (pronated or supinated)"="1", "medium (pronated or supinated)"="2", and "large (pronated or supinated)"="3".

Assessments for the flexibility 447 use a scale from zero to two. The assessments are for the flexibility 447 are for the chest, groin, and/or hamstrings 451 in which "poor flexibility"="0", "average flexibility"="1" and "high flexibility"="2".

Going back to FIG. 4, the measurement totals can be determined (at block 410) after the assessments (block 405). For each plane, the severity numbers within each category are added and a total number is calculated for each plane.

The software can determine the planar order and ratio (block 415) to determine the order and selection of the exercises. Once all planes have been added, the software compares the totals of each plane and orders the totals from the greatest planar disparity to the least planar disparity (e.g., from transverse to frontal to sagittal, or from frontal to transverse to sagittal, etc.). If the planes are equal in weight, the software makes the assessment of order of planes based upon a history of the patient's compensations and session number. For example, if a patient's numbers are equal in all planes, but the patient's greatest disparity up to that point is in the frontal plane, then the software starts with frontal plane exercises.

The software also determines the ratio amongst the planes. In other words, if there is a total planar score of 27 for the transverse plane, 15 for the frontal plane, and 7 for the sagittal plane, then the ratio would be 3:2:1 (e.g., an approximate ratio for 27/15/7). The ratio can be important when looking at the number of exercises allocated to the patient for each plane, because it can help to determine not only the most effective exercises for the patient, but also the most effective exercise within a specific amount depending on the patient's availability. In one example, if the software determines that there should be a total of 7 to 9 exercises based on the average availability of the patient and the ratio is 3:2:1, then there can be 3 or 4 transverse-type exercises, 2 or 3 frontal-type exercises and 1 to 2 sagittal-type exercises.

The software also determines the order and ratio within a plane's measurement types (block 420). Once the overall order has been determined, the software focuses within each plane to determine which category should be dealt with first. For example, if the transverse plane takes precedence and the illiac crest is large, but the PSIS-ASIS disparity and the scapulae elevations are slight, then the software recommends more exercises or attention related to the elevation.

The percentage of exercises chosen per category within each plane is based on the degree of disparity within each category. For example, a medium to large severity may require two or more exercises for that particular deviation. So, for example, if the PSIS-ASIS disparity is large (e.g., a score of 9), then a recommendation for multiple exercises can be generated for that deviation. In another example, when the severity number is slight (e.g., a score of 1 in the frontal plane category), then the software may not generate a recommendation for an exercise for every deviation that is a "1". In some cases, one recommended exercise can deal with multiple, different "slight" deviations.

Determining the ratio may be important within a plane's measurement types. For example, with the above scenario of a patient's ration of 3:2:1, the software can determine that an amount of exercises recommended first can be 3 to 4 transverse exercises. If the illiac crest is a large disparity, and the PSIS-ASIS and the Scapulae Elevation are only slight, then the ratio within this plane could be 2:1:1. Therefore, for this example, the recommendation of 3 or 4 transverse exercises chosen by the software may focus mainly on the PSIS-ASIS by allocating at least 2 or 3 exercises for this measurement type. This determination may be important when looking at the number of exercises allocated to the patient, because the software can not only choose the most effective exercises for the patient, but also the most effective exercise within a specific amount depending on the patient's availability.

Once the order and ratios have been determined (block 420), the exercises chosen for each planar deviation is determined by the software based on five primary variables in the following exemplary order: flexibility (block 425), session number (block 430), ability (block 435), motivation (block 440), and symptoms (block 445). Other embodiments may use other variables or may differ their order of priority.

The software can generate a recommendation of exercises based on a level of flexibility (block 425). The flexibility levels can be assessed for three main areas: chest, groin, and hamstrings. There can be a variety of muscle flexibility tests that can be used in determining the level of flexibility. For example, the categories for the levels of flexibility are as follows: "High Flexibility"="1"; "Average Flexibility"="2"; and "Low Flexibility"="3". The degree of difficulty for each exercise can fluctuate according to the flexibility of individual patients, and can be used to determine the degree of difficulty for each exercise. For example, an Inverted Wall exercise for a patient with poor flexibility in the hamstring category will be much more difficult than for a patient who is very flexible in the hamstring category.

The software can use tables and/or may rely on a database of charts associated with flexibility. In some embodiments of the invention, up to nine different charts may be used in determining the level of difficulty for each exercise as it pertains to a patient's flexibility. Each chart may represent a specific plane and the exercises primarily affecting that plane for the flexibility in question. The software may list the exercises in order of least difficult to most difficult. When determining from which category an exercise can be chosen, the software first determines which measurement type is being addressed and then associates which flexibility area corresponds with that measurement type and what level of flexibility is associated. For example, if the focus is on a spinal offset, then the software focuses specifically on the flexibility associated with the chest area. Once the flexibility area has been determined, the software then chooses an appropriate planar category corresponding to that flexibility. For example, for a patient who has low flexibility in the chest area, the software chooses to use an inflexible sagittal plane chart. As the software provides recommendations for routine sequencing, the same process could continue for each measurement type being addressed. If there are different flexibilities within the same patient, then the software switches among the appropriate charts throughout the exercise routine. The software also utilizes a formatted chart of all the exercises categorized by primary and secondary plane functions along with the degree of difficulty.

Another variable used by the software in developing an exercise routine is a session number and a starting point for each routine (block 430). The patient is assigned a new session number each time they start a new set of exercises. In some embodiments of the invention, there may be up to eight listed categories that correspond with the session number of a patient, to allow for a focused guideline starting point with each session. For example, after the software has chosen an appropriate chart for session one, the software looks in a category to pick a first exercise. For session two, the software looks at another category of the appropriate chart to pick the next exercise, and performs the exercise selections as described above. As a result, the software helps to ensure that the starting demands for each exercise routine for a patient are progressively changing.

Another variable used by the software in writing an exercise routine is an ability of the patient in performing the exercises recommended by the software. In terms of coordination, the coordination abilities of a patient determines which type of exercise is chosen. For example, the patient may have no sense of kinesthetic awareness, even though the patient may be very motivated and highly available. The software is able to provide recommendations to allow the patient's treatment to progress accordingly, but may recommend exercises that are more isometric in nature rather than involving coordinated movements. Alternatively, the software may recommend more difficult exercises in terms of coordination for a top athlete.

Another variable used by the software in writing an exercise routine is the motivation factor (block 440). The motivation of a patient can be used to determine the "ramping" of a routine. "Ramping" corresponds with how quickly the demands of an exercise routine can increase for a patient. For example, a motivated patient with an average availability on session one, can be recommended to ramp quickly to start on category one and end on category eight, with the software selecting eight total exercises. Alternatively, the software may even recommend that a motivated patient ramp quickly by starting on category two and move up only two or three categories (and not all eight categories) based on an assessment of a best outcome for this patient. In another example, an unmotivated patient who is on session two and has minimal availability may be recommended to ramp slowly. For the unmotivated patent, the software may not recommend reaching category eight in the charts, and may only recommend 4 to 6 total exercises.

The software can use several factors associated with determining the patient's motivation, including a persons age, weight, and activity level. The ramping of the routine selected by the software should correlate with the motivation level of the patient.

Another variable used by the software in writing an exercise routine is a variable related to the symptoms of the patient (block 445). The symptoms of the patient's pain, such as the location, frequency, and intensity of the pain, can help to determine a solution to address the pain and form an appropriate exercise routine. In the preferred embodiment, the software can use a symptom level to help create an exercise routine. For example, the symptom level can be used in the software when the pain levels are five and higher, and the position or activity of the exercise can negatively affect the pain level. For instance, if a patient has severe back pain with a pain level of 7 from a herniated disc, and the patient's hips are elevated and the angles skewed, then the software may not recommend rotating the spine. Instead, the software may recommend transverse exercises that could indirectly address these compensations or choose other indirect methods of addressing this disparity. Factors associated with providing exercise solutions for the symptom variable can also include past injuries, surgeries, current diagnoses, and permanent fixtures, such as rods.

The patient's symptoms can be an additional factor to potentially alter the ramping of a routine because the software can use the symptoms variables to override the length and intensity of a routine. For instance, if the patient who has intense pain is highly motivated, highly available, and has high ability, then the software can recommend keeping the ramping of the routine at an even keel instead of ramping the routine aggressively.

Figure 11:
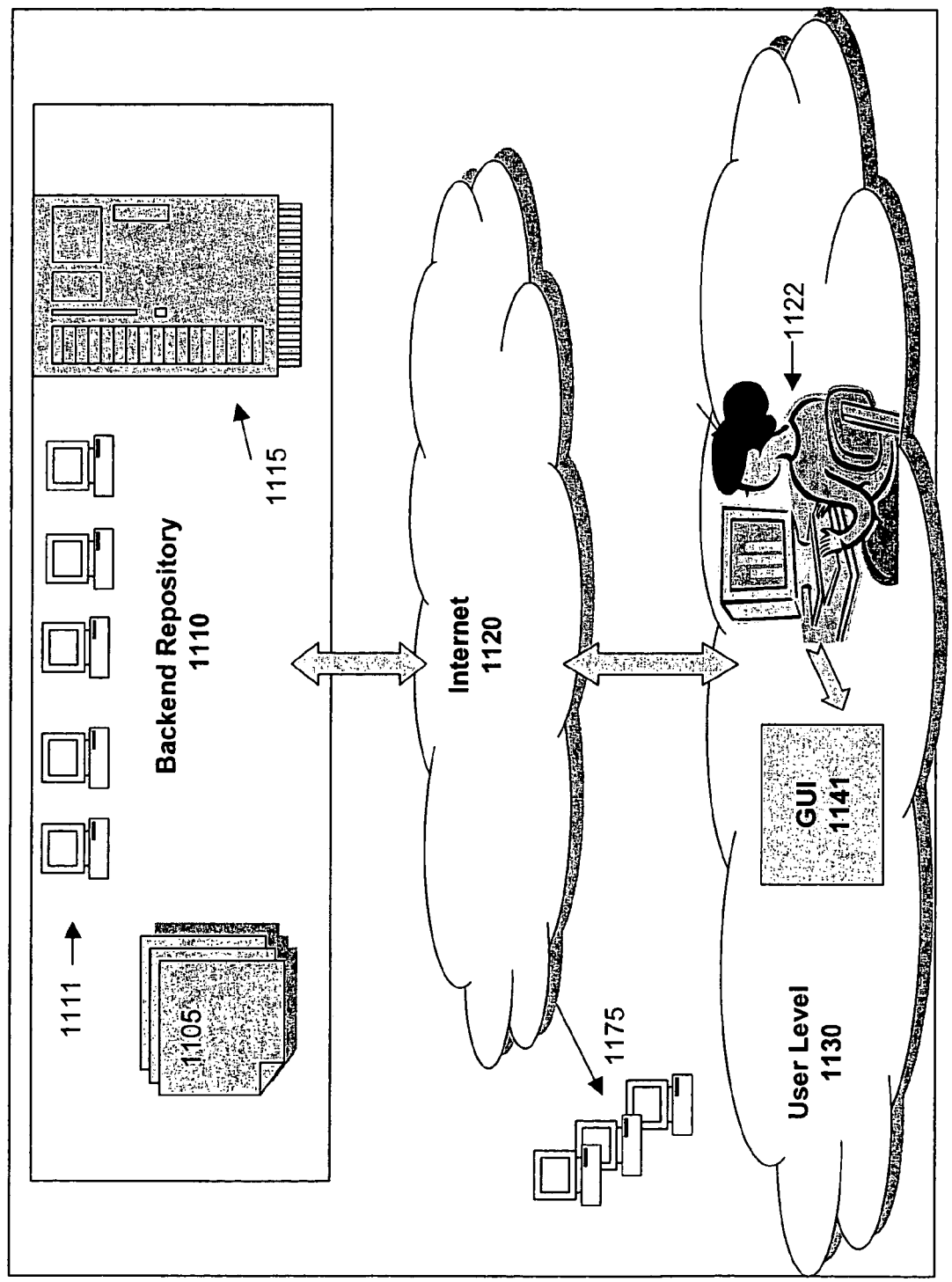
FIG. 11 shows an exemplary diagram for a system to recommend an electronically-generated exercise routine for correcting posture.

FIG. 11 shows diagram one embodiment of the invention for a system to recommend an automatically-generated exercise routine for correcting posture. In general, the system shown in FIG. 11 may be able to store, process, execute, and generate the information discussed above and shown with respect to FIGS. 2-4B. Information for the posture realignment system may be residing in a database 1115 in a backend repository 1110 or may be residing on a physically distributed system, in which the information may reside on the database 1115 and a network of computers 1111.

The information for the posture realignment system may include one or more of the following: (1) business-specific information, such as sales information, patient data information, and data on one or more health care practitioners; (2) data within objects, spreadsheets and text files 1105; and (3) a group of business-related and/or medical-related applications and logic. A program or a process may associate or search for patient data and exercises corresponding to measurements entered by a user 1122 into a user interface 1141 at the user level 1130. The user 1122 can view and/or modify values in user interface 1141.

The exemplary embodiment shown in FIG. 11 shows the backend repository 1110 connected to a user on a client machine over the Internet 1120. Alternatively, the user information, patient information, and exercises may be within a closed system or residing on a single computer. For example, the computer may be a mobile device with memory for exercises and patient information and a processor operable to execute a posture realignment software. The computers 1175 may or may not be networked computers.

Any user 1162, or a group of users, can easily view and/or enter patient data in a graphical user interface. In the case of a single user 1122, for example, the computer may have patient data and information associated with exercises stored in memory or a database residing on the user's computer or available over the Internet from backend repository 1110. In the case of multiple users, patient data, healthcare practitioner data, and exercises, the associated data may be residing in a database 1115 and executing from a server system and accessed by the multiple users. One or more processors may be used to search the database 1115 or the memory on a computer and to execute a computer program product to generate an exercise routine for a given set of patient data entered into the GUI.

Even though one user is shown in FIG. 11, the graphical user interface may be accessed by two or more users. The graphical user interface may use security features (e.g., a password) to permit certain users to edit (e.g., change, add, or delete), information, data, values, and/or recommended exercises. Other users may have read-only access to the graphical user interface and may not be allowed editorial access. The security features may be specific to a role of the health care practitioner. For example, a health care practitioner manager may be allowed to use the graphical user interface to edit patient data, but a health care practitioner trainee may only have read access and may not be able to edit patient data.

In another aspect of the invention, the exercise routines developed for each individual patent can be shown and explained while the patient is in the practitioner's office. As an example, for each exercise selected for a patient, the patient may be shown still pictures or a video of a model patient performing the exercise. An audio facility may be used to add an audio explanation to the still pictures or video, or may be used alone, without still pictures or video. As a take-home item, the patient may be given a hard copy printout describing the exercises, which may include pictures of a model patient performing the exercises. In an alternative embodiment, the user may take home a DVD which has been burned in the practitioner's office containing a customized video of the patient's exercise routine.

The practitioner can communicate with the patient, via email. The email can include descriptions and reminders of the exercises comprising the exercise routine and can include textual descriptions, still pictures, video and audio descriptions of the exercises. The practitioner may additionally send periodic reminders to the patent to remind them to do the exercises. Any email may provide a hyperlink to an Internet web site as described below.

After leaving the practitioner's office, the patient may access, from any computer 1175 having access to Internet 1120, backend repository 1110, if that facility is used by the practitioner to store data. The patient's access to the data will be via a customized web page accessible from any standard Internet browser, such as Microsoft Internet Explorer. The patient's data on the web site will be secured and accessible by the patient upon entry of an appropriate patient identifier and password. As in the practitioner's office, the patient may have the exercise routine explained over the Internet to them via text, still pictures, video, or audio. In addition, there may be a facility available on the web site to log the patient's progress by recording the times and dates that the exercise routine was performed by the patient.

Various implementations of the systems and techniques described herein can be realized in digital electronic circuitry, integrated circuitry, specially designed ASICs (application specific integrated circuits), computer hardware, firmware, software, and/or combinations thereof. These various implementations can include one or more computer programs that are executable and/or interpretable on a programmable system including at least one programmable processor, which may be special or general purpose, coupled to receive data and instructions from, and to transmit data and instructions to, a storage system, at least one input device, and at least one output device.

The software (also known as programs, software tools or code) may include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on one or more computers each having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface, portal, or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), a wireless local area network ("WLAN"), a personal area network ("PAN"), a mobile communication network using a multiple access technology (e.g., a cellular phone network with Code Division Multiple Access, "CDMA"), and the Internet.

The computing system can include clients and servers. A client and server are generally remote from each other and typically interact through a communication network and/or the Internet 1120. The relationship of client and server arises by virtue of computer programs running on the respective computers and having a client-server relationship to each other.

Other tools for obtaining a patient's data may also be used. For example, a tool may be used to obtain objective measurement data from a patient's body using a type of laser other than a plumb laser.

The invention is not limited to the specific embodiments described above. For example, the processes depicted in flow charts and methods herein may be performed in a different order than as depicted and/or stated. Accordingly, other implementations of the software system and/or the measuring tool may be within the scope of the following claims.

APPENDIX

TRANSVERSE PLANE (Average)

1

1) Shin Burners (Static Floor)
2) Shoulder Rotations (Static Floor)
3) Lying Groin Stretch (Active)
4) Wall Groin Stretch
5) Hip Abduction/Adduction
6) Piriformis Stretch (Floor)
7) Lying Leg Rotations
8) Shin Burners (Supine)

2

9) Shin Burners (Free)
10) Piriformis Stretch (Wall)

TRANSVERSE PLANE (Average) —continued

11) Piriformis Stretch (Crossover)
12) Straight Arm Rotations (Buddha's Pose)
13) Shoulder Rotations (Buddha's Pose)
14) Pec Stretch (Buddha's Pose)
15) Prone Scissors

3

16) TFL Stretch (Modified)-NP
17) Rotator Cuff Sequence
18) Elbow Rotations (Extended Floor Position)
19) Prone Scissors (PBF)
20) Hip Circles
21) Striking Cobra (PBF)
22) Pec Stretch (Kneeling)
23) Floor Clock
24) Piriformis Stretch (Elevated Crossover)

4

25) Prone Scissors (Extended)
26) Striking Cobra
27) Straight Arm Rotations (Kneeling)
28) Shoulder Rotations (Kneeling)
29) Elbow Rotations (Wall)
30) Straight Arm Rotations (Standing)
31) Pec Stretch (Standing)
32) Inverted Rotations
33) Lower Spinal Floor Twist

5

34) Intercostal Stretch (Standing)
35) Straight Arm Rotations (Sitting)
36) Shoulder Rotations (Sitting)
37) Pec Stretch (Sitting)
38) Inverted Knee Sequence-NP
39) Sitting Knee Sequence
40) Piriformis Stretch
41) Sitting Leg Rotations

6

42) Shoulder Rotations (Standing)
43) Shoulder Rotations (Heel Drop)
44) Intercostal Stretch (Kneeling)
45) Elevated Femur Rotations (Floor)
46) Elevated Femur Rotations (Wall)
47) Sitting Torso Twist

7

48) Straight Arm Rotations (Floor)
49) Lying Floor Twist,
50) Hurdle Stretch
51) Buddha's Twist
52) Piriformis Stretch (Sitting)
53) Standing Clock

8

54) Hip Circles (3 Positions)
55) Shoulder Sequence
56) TFL Stretch
57) Sitting Side Stretch
58) Kneeling Clock
59) Wall Twist
60) Handle Stretch

TRANSVERSE PLANE (Flexible)

1

5) Shin Burners (Static Floor)
6) Shoulder Rotations (Static Floor)
7) Lying Groin Stretch (Active)
8) Wall Groin Stretch
5) Hip Abduction/Adduction

-continued

TRANSVERSE PLANE (Flexible)

6) Piriformis Stretch (Floor)
7) Lying Leg Rotations
8) Piriformis Stretch (Wall)
9) Piriformis Stretch (Crossover)
10) Prone Scissors

2

11) Shin Burners (Supine)
12) Straight Arm Rotations (Buddha's Pose)
13) Pec Stretch (Buddha's Pose)
14) TFL Stretch (Modified)-NP
15) Rotator Cuff Sequence
16) Prone Scissors (PBF)
17) Striking Cobra (PBF)
18) Pec Stretch (Kneeling)
19) Floor Clock
20) Piriformis Stretch (Elevated Crossover)
21) Lower Spinal Floor Twist

3

22) Shin Burners (Free)
23) Shoulder Rotations (Buddha's Pose)
24) Elbow Rotations (Extended Floor Position)
25) Hip Circles
26) Prone Scissors (Extended)
27) Striking Cobra
28) Straight Arm Rotations (Kneeling)
29) Shoulder Rotations (Kneeling)
30) Inverted Rotations
31) Inverted Knee Sequence-NP
32) Sitting Knee Sequence

4

33) Elbow Rotations (Wall)
34) Straight Arm Rotations (Standing)
35) Pec Stretch (Standing)
36) Intercostal Stretch (Standing)
37) Straight Arm Rotations (Sitting)
38) Shoulder Rotations (Sitting)
39) Pec Stretch (Sitting)
40) Sitting Torso Twist

5

41) Piriformis Stretch
42) Sitting Leg Rotations
43) Shoulder Rotations (Standing)
44) Shoulder Rotations (Heel Drop)
45) Hurdle Stretch

6

46) Intercostal Stretch (Kneeling)
47) Elevated Femur Rotations (Floor)
48) Elevated Femur Rotations (Wall)
49) Buddha's Twist
50) Piriformis Stretch (Sitting)
51) Standing Clock

7

52) Lying Floor Twist
53) Shoulder Sequence
54) TFL Stretch
55) Wall Twist

8

56) Straight Arm Rotations (Floor)
57) Hip Circles (3 Positions)
58) Sitting Side Stretch
59) Kneeling Clock
60) Handle Stretch

TRANSVERSE PLANE (Inflexible)

1

9) Shin Burners (Static Floor)
10) Shoulder Rotations (Static Floor)
11) Hip Abduction/Adduction
12) Lying Leg Rotations

2

5) Lying Groin Stretch (Active)
6) Piriformis Stretch (Floor)
7) Prone Scissors
8) Rotator Cuff Sequence

3

9) Wall Groin Stretch
10) Shin Burners (Supine)
11) Piriformis Stretch (Wall)
12) Piriformis Stretch (Crossover)
13) TFL Stretch (Modified)-NP
14) Elbow Rotations (Extended Floor Position)

4

15) Shin Burners (Free)
16) Prone Scissors (PBF)
17) Hip Circles
18) Pec Stretch (Kneeling)
19) Straight Arm Rotations (Kneeling)

5

20) Straight Arm Rotations (Standing)
21) Pec Stretch (Standing)
22) Straight Arm Rotations (Sitting)
23) Striking Cobra (PBF)

6

24) Floor Clock
25) Shoulder Rotations (Kneeling)
26) Elbow Rotations (Wall)
27) Intercostal Stretch (Standing)

7

28) Sitting Leg Rotations
29) Shoulder Rotations (Standing)
30) Inverted Rotations
31) Lower Spinal Floor Twist
32) Shoulder Rotations (Sitting)

8

33) Pec Stretch (Sitting)
34) Shoulder Rotations (Heel Drop)
35) Elevated Femur Rotations (Floor)
36) Lying Floor Twist,
37) Standing Clock
38) Kneeling Clock
39) Wall Twist

FRONTAL PLANE (Average)

1

1) Floor Presses (Static Floor)
2) Elbow Abduction (Static Floor)
3) Hip Abduction (Static Floor)
4) Hip Adduction (Static Floor)
5) Floor Presses (Hooklying)
6) Floor Presses (Lying Groin)
7) Hip Abduction/Adduction
8) Wall Groin Stretch

2

9) Carpet Glides (Static Floor)
10) Hip Abduction (Hooklying)

| FRONTAL PLANE (Average) |
| --- |
| 11) Hip Adduction (Hooklying) |
| 12) Carpet Glides (Hooklying) |
| 13) Prone Ankle Abduction |
| 14) Prone Ankle Squeeze |
| 15) Side Lateral Raises (Buddha's Pose) |
| 16) Glute Squeezes |
| 3 |
| 17) Ankle/Knee Press (No Lift) |
| 18) Ankle/Knee Opposite Press (No Lift) |
| 19) Prone Ankle Abduction (PBF) |
| 20) Prone Ankle Squeeze (PBF) |
| 21) Prone Opposite Glides |
| 22) Striking Cobra (PBF) |
| 23) Floor Clock |
| 24) Kneeling Ankle Squeeze |
| 25) Kneeling Ankle Press |
| 26) Side Lateral Raises (Kneeling) |
| 4 |
| 27) Striking Cobra |
| 28) Sobriety Glute Squeezes |
| 29) Standing Shrugs (Against Wall)-NP |
| 30) Hip Abduction (Standing) |
| 31) Hip Adduction (Standing) |
| 32) Side Lateral Raises (Standing) |
| 33) Wall Press (Standing) |
| 34) Extended Ankle Press |
| 35) Extended Ankle Press (On Elbows) |
| 36) Extended Ankle Abduction |
| 37) Extended Ankle Abduction (On Elbows) |
| 5 |
| 38) Cobra Ankle Abduction-NP |
| 39) Cobra Ankle Squeeze-NP |
| 40) Arm Glides (Standing) |
| 41) Hip Abduction (Sitting) |
| 42) Hip Adduction (Sitting) |
| 43) Side Lateral Raises (Sitting) |
| 44) Outer Thigh Lifts |
| 45) Lying Side Stretch-NP |
| 6 |
| 46) Hip Abduction (Heel Drop) |
| 47) Hip Adduction (Heel Drop) |
| 48) Wall Press (Heel Drop) |
| 49) Arm Abduction (Heel Drop) |
| 50) Wall Press (Sitting) |
| 51) Elbow Press (Sitting) |
| 52) Inverted Splits |
| 53) Inner Thigh Lifts |
| 7 |
| 54) Arm Glides (Heel Drop) |
| 55) Hip Abduction (Static) |
| 56) Active Hurdle Stretch |
| 57) Carpet Glides (Inverted Wall) |
| 58) Arm Glides (Static Floor Sit) |
| 59) Gluteal Extensions |
| 60) Standing Clock |
| 8 |
| 61) Outer Thigh Lifts (On Elbow)-NP |
| 62) One Arm Bridge-NP |
| 63) Jumping Jacks-NP |
| 64) Military Press (Sitting) |
| 65) Kneeling Clock |
| 66) Standing Splits |
| 67) Triangle |
| 68) Triangle (feet Straight-NP) |
| 68) Extended Triangle |

| FRONTAL PLANE (Flexible) |
| --- |
| 1 |
| 1) Floor Presses (Static Floor) |
| 2) Elbow Abduction (Static Floor) |
| 3) Hip Abduction (Static Floor) |
| 4) Hip Adduction (Static Floor) |
| 5) Floor Presses (Hooklying) |
| 6) Floor Presses (Lying Groin) |
| 7) Hip Abduction/Adduction |
| 8) Wall Groin Stretch |
| 9) Carpet Glides (Static Floor) |
| 10) Hip Abduction (Hooklying) |
| 11) Hip Adduction (Hooklying) |
| 12) Carpet Glides (Hooklying) |
| 13) Glute Squeezes |
| 2 |
| 14) Prone Ankle Abduction |
| 15) Prone Ankle Squeeze |
| 16) Side Lateral Raises (Buddha's Pose) |
| 17) Prone Ankle Abduction (PBF) |
| 18) Prone Ankle Squeeze (PBF) |
| 19) Prone Opposite Glides |
| 20) Striking Cobra (PBF) |
| 21) Floor Clock |
| 22) Side Lateral Raises (Kneeling) |
| 23) Sobriety Glute Squeezes |
| 24) Standing Shrugs (Against Wall)-NP |
| 25) Wall Press (Standing) |
| 26) Lying Sid e Stretch-NP |
| 27) Inverted Splits- |
| 3 |
| 28) Ankle/Knee Press (No Lift) |
| 29) Ankle/Knee Opposite Press (No Lift) |
| 30) Kneeling Ankle Press |
| 31) Kneeling Ankle Squeeze |
| 32) Striking Cobra |
| 33) Side Lateral Raises (Standing) |
| 34) Cobra Ankle Abduction-NP |
| 35) Cobra Ankle Squeeze-NP |
| 36) Arm Glides (Standing) |
| 37) Side Lateral Raises (Sitting) |
| 38) Wall Press (Heel Drop) |
| 39) Carpet Glides (Inverted Wall) |
| 4 |
| 40) Hip Abduction (Standing) |
| 41) Hip Adduction (Standing) |
| 42) Extended Ankle Press (On Elbows) |
| 43) Extended Ankle Abduction (On Elbows) |
| 44) Hip Abduction (Sitting) |
| 45) Hip Adduction (Sitting) |
| 46) Arm Abduction (Heel Drop) |
| 47) Wall Press (Sitting) |
| 48) Elbow Press (Sitting) |
| 49) Arm Glides (Heel Drop) |
| 5 |
| 50) Extended Ankle Press |
| 51) Extended Ankle Abduction |
| 52) Outer Thigh Lifts |
| 53) Hip Abduction (Heel Drop) |
| 54) Hip Adduction (Heel Drop) |
| 55) Inner Thigh Lifts |
| 56) Active Hurdle Stretch |
| 57) Arm Glides (Static Floor Sit) |
| 6 |
| 58) Hip Abduction (Static) |
| 59) Gluteal Extensions |
| 60) Standing Clock |
| 61) Jumping Jacks-NP |
| 7 |
| 62) Military Press (Sitting) |
| 63) Standing Splits |

-continued

FRONTAL PLANE (Flexible)

64) Triangle
65) Triangle (feet Straight-NP)

8

66) Outer Thigh Lifts (On Elbow)-NP
67) One Arm Bridge-NP
68) Kneeling Clock
69) Extended Triangle

FRONTAL PLANE (Inflexible)

1

1) Floor Presses (Static Floor)
2) Hip Abduction (Static Floor)
3) Hip Adduction (Static Floor)
4) Hip Abduction/Adduction
5) Glute Squeezes

2

6) Floor Presses (Hook Lying)
7) Hip Abduction (Hook Lying)
8) Hip Adduction (Hook Lying)
9) Standing Shrugs (Against Wall)-NP

3

10) Elbow Abduction (Static Floor)
11) Floor Presses (Lying Groin)
12) Wall Groin Stretch
13) Carpet Glides (Hook Lying)
14) Prone Ankle Abduction
15) Prone Ankle Squeeze
16) Ankle/Knee Press (No Lift)
17) Ankle/Knee Opposite Press (No Lift)
18) Prone Opposite Glides

4

19) Carpet Glides (Static Floor)
20) Prone Ankle Abduction (PBF)
21) Prone Ankle Squeeze (PBF)
22) Kneeling Ankle Squeeze
23) Kneeling Ankle Press
24) Side Lateral Raises (Kneeling)
25) Sobriety Glute Squeezes
26) Hip Abduction (Standing)
27) Hip Adduction (Standing)
28) Side Lateral Raises (Standing)

5

29) Side Lateral Raises (Buddha's Pose)
30) Striking Cobra (PBF)
31) Floor Clock
32) Wall Press (Standing)
33) Extended Ankle Press
34) Extended Ankle Press (On Elbows)
35) Extended Ankle Abduction
36) Extended Ankle Abduction (On Elbows)
37) Hip Abduction (Sitting)
38) Hip Adduction (Sitting)

6

39) Arm Glides (Standing)
40) Side Lateral Raises (Sitting)
41) Outer Thigh Lifts
42) Lying Side Stretch-NP
43) Hip Abduction (Heel Drop)
44) Hip Adduction (Heel Drop)
45) Wall Press (Heel Drop)
46) Wall Press (Sitting)
47) Inner Thigh Lifts
48) Hip Abduction (Static)

7

-continued

FRONTAL PLANE (Inflexible)

49) Arm Abduction (Heel Drop)
50) Elbow Press (Sitting)
51) Inverted Splits-
52) Arm Glides (Heel Drop)
53) Gluteal Extensions
54) Standing Clock

8

55) One Arm Bridge-NP
56) Jumping Jacks-NP
57) Military Press (Sitting)
58) Standing Splits
59) Triangle
60) Triangle (feet Straight-NP)

SAGITTAL PLANE (Average)

1

1) Static Floor
2) Psoas Stretch (Progressive)
3) Psoas Stretch
4) Psoas Stretch (Rolls)
5) Rolls (Settle)
6) Lying Groin Stretch
7) Blanket Stretch
8) Turtle Pose
9) Abdominal Squeezes (Static Floor)
10) Cervical Stretch
11) Arm Pullovers (Static Floor)
12) Arm Pullovers (Hook lying)
13) Arm Pullovers (Lying Groin)
14) Overhead Press (Static Floor)
15) Overhead Press (Hook lying)-NP
16) Overhead Press (Lying Groin)
17) Pelvic Tilts
18) Shin Burners (Static Floor)
19) Shin Burners (Supine)

2

20) Arm Pullovers (Inverted Wall)
21) Overhead Press (Inverted Wall)
22) Prone Opposite Blocked
23) Prone Blocked Floor
24) Extended Supine
25) Crunches (Static Floor)
26) Shin Burners (Free)
27) Heel-Toe (Block)
28) Heel/Toe (Strap)
29) Cats and Dogs
30) Prone Knee Press
31) Prone Knee Press (Unilateral)
32) Prone Knee Press (Unilateral-PBF)
33) Unilateral Knee Lifts (Hook lying)
34) Buddha's Pose
35) Prone Leg Curls (Block)
36) Prone Leg Curls (Strap)
37) Pec Stretch (Buddha's Pose)
38) Crunches (Lying Groin Stretch)

3

39) Lying Hip Flexor Stretch
40) Abdominal Crunches (Wall)
41) Cobra (On Elbows)
42) Prone Leg Curls (Block-PBF)
43) Prone Leg Curls (Strap-PBF)
44) Kneeling Wall Press
45) Forearm Stretch (Kneeling)
46) Striking Cobra (PBF)
47) Elevated Cats and Dogs
48) Floor Clock

| SAGITTAL PLANE (Average) |
|---|

49) Pec Stretch (Kneeling)
50) Pec Stretch (Standing)
51) Sitting Knee Lifts (Block)
52) Sitting Knee Lifts (Strap)
53) Sitting Knee Lifts (Unilateral)-NP
54) Extended Floor Position (Elbows)
55) Extended Floor Position
56) Overhead Extension (Buddha's Pose)
57) Overhead Extension (Standing)

4

58) Inverted Wall
59) Extended Supine (Ankle/Knee Press)
60) Extended Supine (Ankle/Knee Opposite)
61) Unilateral Hamstring Stretch-NP
62) Lying Calf/Hamstring Stretch
63) Forearm Stretch (Standing)
64) Heel Drop (Wall)
65) Striking Cobra
66) Prone Leg Raise
67) Hip Flexor Abs
68) Heel Raises
69) Kneeling Overhead Stretch (Crossed)
70) Overhead Extension (Kneeling)
71) Inverted Knee Sequence
72) Joggers Stretch (Assisted)
73) Downward Dog (Elevated on Knees)- NP
74) Downward Dog (Modified)
75) Groin Stretch

5

76) Cobra (On Hands)
77) Prone Opposite Lifts
78) Prone Opposite Lifts (Hands & Knees)
79) Pelvic Bridge (Or Active)
80) Piriformis Stretch
81) Free Crunches-NP
82) Hip Thrusts
83) Ankle/Knee Opposite Press (With Lift)
84) Ankle/Knee Press (With Lift)
85) Pec Stretch (Sitting)
86) Sitting Knee Sequence
87) Extended Floor Position (Active)
88) Rolls (Standing)
89) Flamingo Stretch
90) Kneeling Overhead Stretch
91) Sitting Leg Lifts (On Elbows)-NP
92) Groin Stretch (Extended)
93) Standing Leg Curls

6

94) Bicep Curls (Sitting)
95) Bicep Curls (Standing)
96) Heel Drop (Free)
97) Standing Overhead Reach
98) Heel Raises (SOHS)-NP
99) Overhead Extension (Sitting)
100) Knee Extensions
101) Piriformis Stretch (Sitting)
102) Sitting Leg Lifts (Floor)
103) Standing Clock
104) Joggers Stretch
105) Downward Dog
106) Downward Dog (Elevated on Elbows)
107) Extended Floor
108) Static Floor Sit
109) Push-ups (Knees)-NP
110) Buddha's Squat
111) Rooster's Pose

7

112) Sitting Leg Lifts (Wall)
113) Pelvic Tilts (Feet Suspended)-NP
114) Kneeling Clock
115) Extended Floor (Elbows)
116) Extended Floor (On Feet)-NP
117) Donkey Kicks

| SAGITTAL PLANE (Average) |
|---|

118) Free Fall
119) Elevated Blocked Floor
120) Pec Stretch (Floor)-NP
121) Prone Blocked Floor (Elevated)-NP
122) Overhead Extension (Floor)-NP
123) Rooster's Pose (Arms Extended)
124) Buddha's Squat (Static)
125) Step-Ups
126) Kneeling Hamstring Curls-NP
127) Kneeling Overhead Extension (Wall)
128) Reverse Sit-ups-NP
129) Static Lunges-NP

8

130) Plow-NP
131) Core Abs.
132) Duck Walks
133) Free Squat
134) Full Sit-Ups
135) Static Sit-Up
136) Push-ups (Walking Out)
137) Roller Coasters-NP
138) Sit to Stands
139) Inch Worms-NP
140) Full Back Bend
141) Wall Sit
142) Wall Sit (Roll)-Use Wall Sit
143) Extended Squat-NP
144) Squat
145) Full Squat
146) Handstand
147) Decline Wall Sit

| SAGITTAL PLANE (Flexible) |
|---|

1

1) Static Floor
2) Psoas Stretch (Progressive)
3) Psoas Stretch
4) Psoas Stretch (Rolls)
5) Rolls (Settle)
6) Lying Groin Stretch
7) Blanket Stretch
8) Turtle Pose
9) Abdominal Squeezes (Static Floor)
10) Cervical Stretch
11) Arm Pullovers (Static Floor)
12) Arm Pullovers (Hook lying)
13) Arm Pullovers (Lying Groin)
14) Overhead Press (Static Floor)
15) Overhead Press (Hook lying)-NP
16) Overhead Press (Lying Groin)
17) Pelvic Tilts
18) Shin Burners (Static Floor)
19) Prone Opposite Blocked
20) Prone
21) Cats and Dogs
22) Buddha's Pose

2

23) Shin Burners (Supine)
24) Arm Pullovers (Inverted Wall)
25) Overhead Press (Inverted Wall)
26) Lying Hip Flexor Stretch
27) Cobra (On Elbows)
28) Extended Supine
29) Crunches (Static Floor)
30) Heel-Toe (Block)
31) Heel/Toe (Strap)
32) Striking Cobra (PBF)
33) Prone Knee Press

SAGITTAL PLANE (Flexible)

- 34) Prone Knee Press (Unilateral)
- 35) Prone Knee Press (Unilateral-PBF)
- 36) Unilateral Knee Lifts (Hook lying)
- 37) Floor Clock
- 38) Pec Stretch (Buddha's Pose)
- 39) Crunches (Lying Groin Stretch)
- 40) Pec Stretch (Kneeling)
- 41) Overhead Extension (Buddha's Pose)
- 42) Inverted Wall
- 43) Unilateral Hamstring Stretch-NP
- 44) Lying Calf/Hamstring Stretch

3

- 45) Shin Burners (Free)
- 46) Abdominal Crunches (Wall)
- 47) Prone Leg Curls (Block)
- 48) Kneeling Wall Press
- 49) Forearm Stretch (Kneeling)
- 50) Prone Leg Curls (Strap)
- 51) Elevated Cats and Dogs
- 52) Forearm Stretch (Standing)
- 53) Heel Drop (Wall)
- 54) Striking Cobra
- 55) Kneeling Overhead Stretch (Crossed)
- 56) Overhead Extension (Kneeling)
- 57) Inverted Knee Sequence
- 58) Joggers Stretch (Assisted)
- 59) Downward Dog (Elevated on Knees)- NP
- 60) Groin Stretch
- 61) Cobra (On Hands)
- 62) Sitting Knee Sequence
- 63) Extended Floor Position (Elbows)
- 64) Overhead Extension (Standing)

4

- 65) Prone Leg Curls (Block-PBF)
- 66) Prone Leg Curls (Strap-PBF)
- 67) Pec Stretch (Standing)
- 68) Sitting Knee Lifts (Block)
- 69) Sitting Knee Lifts (Strap)
- 70) Sitting Knee Lifts (Unilateral)-NP
- 71) Extended Floor Position
- 72) Extended Supine (Ankle/Knee Press)
- 73) Extended Supine (Ankle/Knee Opposite)
- 74) Prone Leg Raise
- 75) Hip Flexor Abs
- 76) Heel Raises
- 77) Downward Dog (Modified)
- 78) Prone Opposite Lifts
- 79) Hip Thrusts
- 80) Pec Stretch (Sitting)
- 81) Extended Floor Position (Active)
- 82) Flamingo Stretch
- 83) Kneeling Overhead Stretch
- 84) Sitting Leg Lifts (On Elbows)-NP
- 85) Standing Leg Curls
- 86) Joggers Stretch

5

- 87) Prone Opposite Lifts (Hands & Knees)
- 88) Pelvic Bridge (Or Active)
- 89) Piriformis Stretch
- 90) Free Crunches-NP
- 91) Ankle/Knee Opposite Press (With Lift)
- 92) Ankle/Knee Press (With Lift)
- 93) Rolls (Standing)
- 94) Groin Stretch (Extended)
- 95) Standing Overhead Reach
- 96) Overhead Extension (Sitting)
- 97) Knee Extensions
- 98) Downward Dog
- 99) Static Floor Sit

6

- 100) Bicep Curls (Sitting)
- 101) Bicep Curls (Standing)
- 102) Heel Drop (Free)
- 103) Heel Raises (SOHS)-NP
- 104) Piriformis Stretch (Sitting)
- 105) Sitting Leg Lifts (Floor)
- 106) Standing Clock
- 107) Downward Dog (Elevated on Elbows)
- 108) Extended Floor
- 109) Push-ups (Knees)-NP
- 110) Buddha's Squat
- 111) Rooster's Pose
- 112) Elevated Blocked Floor
- 113) Pec Stretch (Floor)-NP
- 114) Prone Blocked Floor (Elevated)-NP
- 115) Overhead Extension (Floor)-NP

7

- 116) Sitting Leg Lifts (Wall)
- 117) Pelvic Tilts (Feet Suspended)-NP
- 118) Extended Floor (Elbows)
- 119) Donkey Kicks
- 120) Free Fall
- 121) Rooster's Pose (Arms Extended)
- 122) Buddha's Squat (Static)
- 123) Step-Ups
- 124) Kneeling Hamstring Curls-NP
- 125) Kneeling Overhead Extension (Wall)
- 126) Reverse Sit-ups-NP
- 127) Static Lunges-NP
- 128) Plow-NP
- 129) Inch Worms-NP

8

- 130) Kneeling Clock
- 131) Extended Floor (On Feet)-NP
- 132) Core Abs.
- 133) Duck Walks
- 134) Free Squat
- 135) Full Sit-Ups
- 136) Static Sit-Up
- 137) 9 Push-ups (Walking Out)
- 138) Roller Coasters-NP
- 139) Sit to Stands
- 140) Full Back Bend
- 141) Wall Sit
- 142) Wall Sit (Roll)-Use Wall Sit
- 143) Extended Squat-NP
- 144) Squat
- 145) Full Squat
- 146) Handstand
- 147) Decline Wall Sit

SAGITTAL PLANE (Inflexible)

1

- 1) Static Floor
- 2) Psoas Stretch (Progressive)
- 3) Abdominal Squeezes (Static Floor)
- 4) Cervical Stretch
- 5) Arm Pullovers (Static Floor)
- 6) Shin Burners (Static Floor)

2

- 7) Pelvic Tilts
- 8) Arm Pullovers (Hook lying)
- 9) Lying Groin Stretch
- 10) Psoas Stretch
- 11) Cats and Dogs
- 12) Prone Knee Press
- 13) Unilateral Knee Lifts (Hook lying)

3

- 14) Psoas Stretch (Rolls)

-continued

| | SAGITTAL PLANE (Inflexible) |
|---|---|
| 15) | Blanket Stretch |
| 16) | Arm Pullovers (Lying Groin) |
| 17) | Overhead Press (Static Floor) |
| 18) | Shin Burners (Supine) |
| 19) | Prone Opposite Blocked |
| 20) | Prone Blocked Floor |
| 21) | Heel-Toe (Block) |
| 22) | Heel/Toe (Strap) |
| 23) | Prone Leg Curls (Block) |
| 24) | Prone Leg Curls (Strap) |
| 25) | Lying Hip Flexor Stretch |

4

| 26) | Rolls (Settle) |
|---|---|
| 27) | Overhead Press (Hook lying)-NP |
| 28) | Extended Supine |
| 29) | Crunches (Static Floor) |
| 30) | Shin Burners (Free) |
| 31) | Prone Knee Press (Unilateral) |
| 32) | Cobra (On Elbows) |
| 33) | Prone Leg Curls (Block-PBF) |
| 34) | Prone Leg Curls (Strap-PBF) |
| 35) | Striking Cobra (PBF) |
| 36) | Sitting Knee Lifts (Block) |
| 37) | Sitting Knee Lifts (Strap) |
| 38) | Sitting Knee Lifts (Strap) |
| 39) | Downward Dog (Elevated on Knees)-NP |

5

| 40) | Overhead Press (Lying Groin) |
|---|---|
| 41) | Crunches (Lying Groin Stretch) |
| 42) | Abdominal Crunches (Wall) |
| 43) | Kneeling Wall Press |
| 44) | Floor Clock |
| 45) | Pec Stretch (Kneeling) |
| 46) | Sitting Knee Lifts (Unilateral)-NP |
| 47) | Extended Floor Position |
| 48) | Extended Supine(Ankle/Knee Press) |
| 49) | Extended Supine(Ankle/Knee Opposite) |
| 50) | Forearm Stretch (Standing) |
| 51) | Heel Raises |
| 52) | Kneeling Overhead Stretch (Crossed) |
| 53) | Joggers Stretch (Assisted) |
| 54) | Ankle/Knee Opposite Press (With Lift) |
| 55) | Ankle/Knee Press (With Lift) |
| 56) | Pec Stretch (Sitting) |
| 57) | Rolls (Standing) |
| 58) | Prone Knee Press (Unilateral-PBF) |

6

| 59) | Forearm Stretch (Kneeling) |
|---|---|
| 60) | Elevated Cats and Dogs |
| 61) | Pec Stretch (Standing) |
| 62) | Extended Floor Position (Elbows) |
| 63) | Hip Flexor Abs |
| 64) | Groin Stretch |
| 65) | Cobra (On Hands) |
| 66) | Prone Opposite Lifts |
| 67) | Free Crunches-NP |
| 68) | Extended Floor Position (Active) |
| 69) | Flamingo Stretch |
| 70) | Kneeling Overhead Stretch |
| 71) | Overhead Extension (Kneeling) |

7

| 72) | Unilateral Hamstring Stretch-NP |
|---|---|
| 73) | Lying Calf/Hamstring Stretch |
| 74) | Heel Drop (Wall) |
| 75) | Prone Leg Raise |
| 76) | Prone Opposite Lifts (Hands & Knees) |
| 77) | Pelvic Bridge (Or Active) |
| 78) | Sitting Leg Lifts (On Elbows)-NP |
| 79) | Groin Stretch (Extended) |
| 80) | Heel Drop (Free) |
| 81) | Standing Overhead Reach |
| 82) | Overhead Extension (Sitting) |
| 83) | Knee Extensions |

-continued

| | SAGITTAL PLANE (Inflexible) |
|---|---|
| 84) | Standing Clock |
| 85) | Extended Floor |
| 86) | Push-ups (Knees)-NP |
| 87) | Donkey Kicks |
| 88) | Free Fall |
| 89) | Elevated Blocked Floor |
| 90) | Step-Ups |
| 91) | Static Lunges-NP |

8

| 92) | Sitting Leg Lifts (Floor) |
|---|---|
| 93) | Rooster's Pose |
| 94) | Sitting Leg Lifts (Wall) |
| 95) | Pelvic Tilts (Feet Suspended)-NP |
| 96) | Buddha's Squat (Static) |
| 97) | Core Abs. |
| 98) | Free Squat |
| 99) | Full Sit-Ups |
| 100) | Static Sit-Up |
| 101) | Push-ups (Walking Out) |
| 102) | Sit to Stands |
| 103) | Wall Sit |
| 104) | Wall Sit (Roll)-Use Wall Sit |
| 105) | Squat |
| 106) | Full Squat |
| 107) | Decline Wall Sit |

What is claimed is:

1. A tool to obtain measurements on a human body, the tool comprising:
    a level configured to indicate an angle with respect to ground, wherein said level includes a scale extending longitudinally across the level;
    a protractor configured for measuring angles, wherein said protractor is attached substantially in the center of said level and parallel to said scale;
    a laser mount attached in the center of said level, wherein said laser mount is configured to hold a laser;
    two caliper arms each with a proximal end rotatably attached to the center of said level, wherein each of said caliper arms is configured to extend from said center of said level, and wherein said caliper arms are configured to move at an angle measurable with said protractor; and
    two finger rings, one ring attached to the distal end of each of said caliper arms.

2. The tool of claim 1 wherein said scale includes ruler-like gridlines.

3. The tool of claim 2 further comprising a laser attached to the laser mount.

4. The tool of claim 3 wherein said laser mount is configured to hold said laser such that said laser projects a laser beam from the center of said level, such that said laser beam is perpendicular to said longitudinal scale.

5. The tool of claim 4 wherein each of said caliper arms rotates at least approximately 90 degrees from the center of said level.

6. The tool of claim 5 further comprising a set of two slideable caliper arms attached to said level, wherein a proximal end of each slideable caliper arm is attached to said level, wherein the set of slideable caliper arms are configured to move parallel to said level, and wherein a scale displays the distance between said slideable caliper arms.

7. The tool of claim 6 further comprising a handle attached between each rotatable caliper arm and said finger ring.

8. An apparatus to measure offsets and displacements associated with human body parts, the apparatus comprising:
- a level including a longitudinal scale for measuring a length in a longitudinal direction, wherein said level also including a level indicator to indicate an angle of said level with respect to ground;
- a pair of sliding arms connected to said level and extending perpendicularly therefrom, wherein the length between said sliding arms is measurable on said scale, and wherein said sliding arms are configured to slide parallel to the longitudinal direction of said longitudinal scale;
- a protractor attached to a middle section of said level, wherein the center of said protractor is approximately at the center of said scale;
- a pair of rotating caliper arms connected to said level at a proximal end and extending from a middle section of said level, wherein said protractor includes markings to indicate an angle between said pair of rotating calipers arms.

9. The apparatus of claim 8 further comprising a laser attachment mechanism for attaching a laser to said level.

10. The apparatus of claim 9 wherein said laser attachment mechanism comprises a strap to secure a laser.

11. The apparatus of claim 10 wherein said laser is a plumb laser.

12. The apparatus of claim 11 wherein said laser projects a laser beam approximately perpendicular to the direction of said scale.

* * * * *